(12) United States Patent
Tate

(10) Patent No.: US 7,904,252 B2
(45) Date of Patent: Mar. 8, 2011

(54) METHOD FOR MEASURING A STRUCTURAL CHANGE IN A PROTEIN

(75) Inventor: Shin-ichi Tate, Suita (JP)

(73) Assignee: Hitachi, Ltd., Tokyo (JP)

( * ) Notice: Subject to any disclaimer, the term of this patent is extended or adjusted under 35 U.S.C. 154(b) by 847 days.

(21) Appl. No.: 10/580,427

(22) PCT Filed: Nov. 26, 2004

(86) PCT No.: PCT/JP2004/017626
§ 371 (c)(1),
(2), (4) Date: May 30, 2007

(87) PCT Pub. No.: WO2005/052620
PCT Pub. Date: Jun. 9, 2005

(65) Prior Publication Data
US 2007/0250298 A1    Oct. 25, 2007

(30) Foreign Application Priority Data

Nov. 28, 2003    (JP) .................................. 2003-400864

(51) Int. Cl.
*G01N 31/00*    (2006.01)
(52) U.S. Cl. ............. 702/27; 702/19; 702/150; 702/189; 703/2; 703/11
(58) Field of Classification Search .......................... None
See application file for complete search history.

(56) References Cited

FOREIGN PATENT DOCUMENTS

| JP | 11-513498 | 11/1996 |
|---|---|---|
| JP | 2001-321192 | 5/2000 |
| JP | 2003-130823 | 10/2001 |
| WO | WO 97/18471 | * 5/1997 |

OTHER PUBLICATIONS

Alba et al., "NMR dipolar couplings for the structure determination of biopolymers in solution", 2002, Progress in Nuclear Magnetic Resonance Spectroscopy, vol. 40, 2002, pp. 175-197.*
Tate et al., "Molecular-orientation analysis based on alignment-induced TROSY chemical shift changes", 2004, Journal of Magnetic Resonance, vol. 171, pp. 284-292.*
Suzanne B. Shuker et al., "Discovering High-Affinity Ligands for Proteins: SAR by NMR", Science, vol. 274, Nov. 29, 1996, pp. 1531-1534.
Ichio Shimada, "Structure Analysis of High-Molecular Proteins by NMR", Pharmacia, vol. 31 (1995) in Japanese with partial translation, pp. 1371-1375.

* cited by examiner

*Primary Examiner* — Carolyn L. Smith
(74) *Attorney, Agent, or Firm* — Stites & Harbison, PLLC; Juan Carlos A. Marquez, Esq.

(57) ABSTRACT

A method of easily and speedily determining what structural change is experienced by a target protein upon contact and binding of any arbitrary compound to the target protein; a method of selecting and screening a compound for use in the method; and a computer program for carrying out these methods. In one embodiment, a Saupe order matrix element of domain is obtained from atomic coordinates of domain and an axial-direction variation of NMR signal dependent upon the orientation angle of molecule in magnetic field, and the matrix is diagonalized to thereby obtain the orientation information on the domain. Using of any change of the orientation information as an indicator for structural change enables realization of the intended easy and speedy measurement of structural change of the target protein.

11 Claims, 8 Drawing Sheets

(a)

$DOC = a^2 + b^2 + c^2$ (b)

$DOS = a^2 + b^2 + c^2$

METHOD FOR MEASURING A STRUCTURAL CHANGE IN A PROTEIN

TECHNICAL FIELD

The present invention relates to a method of measuring a structural variation in a protein when a compound is bound to the protein by use of nuclear magnetic resonance, a method of selecting a particular compound based on such structural variations, and a program for use in the methods.

BACKGROUND ART

When cells respond to extracellular stimuli, various proteins in the cells are involved in the response. Thus, agonists and/or antagonists targeting such proteins may be used as lead compounds for novel drugs.

Conventional methods of searching for agonists and/or antagonists to a protein include searching by use of physical binding to the target protein as indicator and searching by use of capacity to induce a biological reaction involving the target protein (functional induction capacities) as indicator.

In the method of searching by use of physical binding to the target protein as indicator, compounds from a compound library (e.g., a combination library) are examined for strength of binding to the target protein, number of bound molecules per molecule thereof and so forth, and then high-affinity compounds to the target protein above a certain reference affinity are screened.

On the other hand, in the method using functional induction capacity for the target protein, namely, a biological reaction involving the target protein, as indicator, compounds from a compound library (e.g., a combination library) are contacted with cells expressing the target protein and the resulting variations in the biological reaction (for example, qualitative variations such as initiation and termination of the biological reaction, or quantitative variations such as increased or decreased degree of the biological reaction) are examined as indicator. To carry out the method using functional induction capacity as indicator, it is required to establish an assay system specific to an individual target protein. As a consequence, when the effect of the compound is analyzed, for example, for living cells, there are such limitations that its reliability and experimental accuracy may depend on the assay system.

Agonists and/or antagonists to the protein are identified and the identified compounds can be used as lead compound for a novel drug. In screening candidate compounds for a novel drug, it is useful to see how the conformation of the target protein is varied by their binding to the target protein. It is because such information of conformational variations may provide a clue to the design of a candidate drug having a more appropriate structure.

However, in either case of physical binding or functional induction capacity used as indicator, the state of binding of the compound to the protein is not directly observed. Therefore, the structure and function of the compound is speculated by analogy from the binding capacity or functional induction capacity for the target protein provided as indirect observation. Simple determination of the presence or absence of physical binding or functional induction capacity may hardly reveal the real state of interaction between the target protein and the compound and may not always provide a clear guide for drug design.

In order to eliminate such problems presented by conventional assay methods, an assay method utilizing nuclear magnetic resonance (NMR) has been published in which binding of a compound to the functional site of a target protein is confirmed by NMR (Shuker S. B. et al., Science (1996) 274, 1531-1534) (JP-A-2001-321192). In this technique of prior art, such a case that the compound is non-specifically bound to a non-functional site of the target protein can be excluded, and lead compounds can be thus identified more efficiently than in the conventional assay of physical binding which has a difficulty in distinguishing between nonspecific binding and specific binding. However, the technique is not suitable to measure a structural variation itself in the protein, though it enables the binding site to be identified. Therefore, this technique is effective to design inhibitors capable of binding to the active site of the target protein, but is not so effective to design agonistic agents (e.g., agonists) capable of inducing the activity of the protein. Since identification of an agonistic lead compound requires to screen compounds of interest by seeing if they bind properly to the binding site on the target protein to its substrate and further induce the active structure of the target protein, this conventional technique has not been adequate to identify the agonistic lead compound.

It can be determined by structural analysis based on X-ray crystallography if a compound can induce the active structure of a target protein. However, the X-ray crystallographical structural analysis is not suitable for efficient screening since it needs enormous amounts of labor and time to crystallize many compounds together with the target protein and analyze the conformation of as many crystals. Consequently, a simple and rapid method to determine a structural change in the target protein, which may occur when an arbitrary compound is contacted with the target protein and bound thereto, and a computer program to carry out the method are needed.

Patent Document 1: JP-A-2001-321192.

Non-Patent Document 1: Shuker S. B. et al., Science (1996) 274, 1531-1534.

DISCLOSURE OF THE INVENTION

Problems to be Solved by the Invention

The subject of the present invention is to provide a simple and rapid method of determining a structural change in the target protein, which may occur when an arbitrary compound is contacted with the target protein and bound thereto, a method of screening compounds for selection by using the above mentioned method and a computer program to carry out those methods.

It is one subject of the present invention to provide a method of measuring a structural change in a protein, which may occur when an arbitrary compound is contacted with the protein and bound thereto, for example, using nuclear magnetic resonance. It is also one subject of the present invention to provide a method of identifying an arbitrary compound for screening which may induce a structural change in a protein when the compound is contacted with the protein and bound thereto. It is another subject of the present invention to provide a method of identifying a compound for screening which induces a structural change in a protein similar to that induced by a ligand or an agonist, by comparing a structural change in the protein when an arbitrary compound is bound thereto with a structural change in the same protein when such a compound as a ligand or an agonist is bound thereto, which is known to induce a structural change in a protein when it is bound to the protein.

It is a further subject of the present invention to provide a computer program used in these methods.

Means for Solving the Problems

The present inventors have developed a method of estimating a conformational change in a target protein, which is induced by addition of a compound into a solution of the target protein, by a change thereof in a TROSY correlation NMR spectrum (for example, $^1$H/$^{15}$N NMR spectrum) and a program therefor, and completed the present invention thereby. The present inventors have developed a novel method capable of concurrent observation of both of 1) a site on a target protein to which a compound is bound, and 2) a structural change in the target protein induced by the compound, resulting in the completion of the invention.

Thus, the present invention provides the following:

1. A method of measuring a structural change in a protein when the protein is contacted with a compound, comprising the steps of:
  (a) selecting a domain in the protein;
  (b) providing information on an orientation of the domain when the protein is not in contact with the compound;
  (c) providing information on an orientation of the domain when the protein is in contact with the compound, by
    (i) providing known atomic coordinates for the domain,
    (ii) providing axial variations of NMR signals, which are generated from the protein in contact with the compound in the presence of a liquid crystalline material by two-dimensional TROSY NMR spectroscopy and depend on an orientation angle of the molecules in a magnetic field,
    (iii) determining Saupe order matrix elements for the domain from the atomic coordinates for the domain and the axial variations of NMR signals, and
    (iv) diagonalizing the determined matrix to produce the information on an orientation of the domain; and
  (d) measuring the structural change in the protein by a difference between the information on an orientation provided in step (b) and the information on an orientation provided in step (c);

2. The method of measurement according to item 1, wherein the step (b) is a step of:
  (b) providing the information on an orientation of the domain when the protein is not in contact with the compound, by
    (v) providing known atomic coordinates for the domain,
    (vi) providing axial variations of NMR signals, which are generated from the protein in no contact with the compound in the presence of the liquid crystalline material by two-dimensional TROSY NMR spectroscopy and depend on the orientation angle of the molecules in the magnetic field,
    (vii) determining Saupe order matrix elements for the domain from the atomic coordinates for the domain and the axial variations of NMR signals, and
    (viii) diagonalizing the determined matrix to produce the information on an orientation of the domain;

3. The method of measurement according to item 1, wherein the step (b) is a step of
  (b) providing the information on an orientation of the domain from the atomic coordinates provided previously when the protein is not in contact with the compound;

4. The method of measurement according to item 1, wherein in the step (c), the axial variations of NMR signals, which are generated by two-dimensional TROSY NMR spectroscopy and depend on the orientation angle of the molecules in the magnetic field, are variations along a $^{15}$N axis;

5. The method of measurement according to item 4, wherein the Saupe order matrix elements in (iii) are determined by:
  with respect to the kth pair of $^{15}$N nuclear spins in the domain,
  providing $\phi^k_i$ as a vector angle of an N—H bond having the kth pair of spins in the domain to the ith molecular axis,
  providing $\phi^k_j$ as a vector angle of an N—H bond having the kth pair of spins in the domain to the jth molecular axis,
  setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å,
  determining as $\delta_{ij}$ a tensor value for chemical shift anisotropy of a $^{15}$N nucleus in an arbitrary residue of the protein, and
  determining the Saupe order matrix elements $S_{ij}$ defining the molecular orientation with respect to the magnetic field, by contacting the protein with the compound in the presence of the liquid crystalline material, providing $\Delta\delta\text{trosy}(k)$ for the kth pair of $^{15}$N nuclear spins by two-dimensional TROSY NMR spectroscopy, and using the $\Delta\delta\text{trosy}(k)$ together with the following equation (1):

$$\Delta\delta trosy(k) = \Sigma S_{ij}\{0.5 D^0_{nh} \cos\phi^k_i \cos\phi^k_j + (2/3)\delta_{ij}\} \qquad (1)$$

i, j=x, y, z;

6. The method of measurement according to item 2, wherein in the step (b), the axial variations of NMR signals, which are generated by two-dimensional TROSY NMR spectroscopy and depend on the orientation angle of the molecules in the magnetic field, are variations along a $^{15}$N axis;

7. The method of measurement according to item 6, wherein the Saupe order matrix elements in (vii) are determined by:
  with respect to the kth pair of $^{15}$N nuclear spins in the domain,
  providing $\phi^k_i$ as a vector angle of an N—H bond having the kth pair of spins in the domain to the ith molecular axis,
  providing $\phi^k_j$ as a vector angle of an N—H bond having the kth pair of spins in the domain to the jth molecular axis,
  setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å,
  determining as $\delta_{ij}$ a tensor value for chemical shift anisotropy of a $^{15}$N nucleus in an arbitrary residue of the protein, and
  determining the Saupe order matrix elements $S_{ij}$ defining the molecular orientation with respect to the magnetic field, by making no contact of the protein with the compound in the presence of the liquid crystalline material, providing $\Delta\delta\text{trosy}(k)$ for the kth pair of $^{15}$N nuclear spins by two-dimensional TROSY NMR spectroscopy, and using the $\Delta\delta\text{trosy}(k)$ together with the following equation (1):

$$\Delta\delta trosy(k) = \Sigma S_{ij}\{0.5 D^0_{nh} \cos\phi^k_i \cos\phi^k_j + (2/3)\delta_{ij}\} \qquad (1)$$

i, j=x, y, z;

8. The method according to item 5 or 7, wherein a structural change in the protein when the protein and the compound are contacted is digitized as degree of orientational change by:
  (ix) providing directions of orientation tensor axes by a first three unit vectors perpendicular to each other, by using the information on an orientation of the domain in the protein before the protein is contacted with the compound, wherein the first three unit vectors are expressed by $$\vec{e}_{fx}, \quad \vec{e}_{fy}, \quad \vec{e}_{fz}$$

(x) providing directions of orientation tensor axes by a second three unit vectors perpendicular to each other, by using the information on an orientation of the domain in the protein after the protein is contacted with the compound, wherein the second three unit vectors are expressed by $$\vec{e}_{bx}, \vec{e}_{by}, \vec{e}_{bz}$$

(xi) denoting respective angles between the individual first unit vectors and the individual second unit vectors by a, b and c, and (xii) giving a degree of orientational change by the following equation:

degree of orientational change=$a^2+b^2+c^2$;

9. The method according to item 2, further comprising a step of identifying a position on the protein to which the compound is bound;

10. The method according to item 9, wherein the step of identifying a position on the protein to which the compound is bound is carried out by comparing the two-dimensional TROSY NMR spectrum obtained in the step (b) with the two-dimensional TROSY NMR spectrum obtained in the step (c) to detect a spectral change, and identifying an amino acid residue in the protein which has induced the spectral change;

11. The method according to item 1, wherein the liquid crystalline material comprises a mixture selected from the following group:

a mixture of dimyristoylphosphatidylcholine (DMPC) and dihexanoylphosphatidylcholine (DHPC), a mixture of dimyristoylphosphatidylcholine (DMPC), dihexanoylphosphatidylcholine (DHPC), and sodium dodecyl sulfate (SDS), a mixture of dimyristoylphosphatidylcholine (DMPC), dihexanoylphosphatidylcholine (DHPC), and cetyltrimethylammonium bromide (CTAB), a mixture of 1,2-di-O-dodecyl-sn-glycero-3-phosphocholine (DIODPC) and 3-(cholamidepropyl)-dimethylammonio-2-hydroxy-1-propane sulfate (CHAPS), a mixture of n-alkyl-poly(ethyleneglycol)/n-alkylalcohol, filamentous phage, a mixture of cetylpyridinium chloride (CPCl)-hexanol-NaCl, a mixture of cetylpyridinium bromide (CPBr)-hexanol-NaCl, a purple membrane fragment of *Halobacterium* spp., microcrystalline cellulose, and polyacrylamide gel;

12. The method according to item 11, wherein the liquid crystalline material is the mixture of 7.5% (w/v) composed of dimyristoylphosphatidylcholine (DMPC), dihexanoylphosphatidylcholine (DHPC), and cetyltrimethylammonium bromide (CTAB);

13. A method of selecting a compound capable of inducing a structural change in a domain within a protein when the protein is contacted with the compound, comprising the steps of:

(a) selecting a domain in the protein;

(b) providing information on an orientation of the domain when the protein is not in contact with the compound;

(c) providing information on an orientation of the domain when the protein is in contact with the compound, by (i) providing known atomic coordinates for the domain, (ii) providing axial variations of NMR signals, which are generated from the protein in contact with the compound in the presence of a liquid crystalline material by two-dimensional TROSY NMR spectroscopy and depend on an orientation angle of the molecules in a magnetic field, (iii) determining Saupe order matrix elements for the domain from the atomic coordinates for the domain and the axial variations of NMR signals, and (iv) diagonalizing the determined matrix to produce the information on an orientation of the domain; and (d) determining if the compound is capable of inducing a structural change in the domain when the protein is contacted with the compound, by making a comparison between the information on an orientation provided in step (b) and the information on an orientation provided in step (c);

14. The method according to item 13, wherein the step (b) is a step of:

(b) providing the information on an orientation of the domain when the protein is not in contact with the compound, by (v) providing known atomic coordinates for the domain, (vi) providing axial variations of NMR signals, which are generated from the protein in no contact with the compound in the presence of the liquid crystalline material by two-dimensional TROSY NMR spectroscopy and depend on the orientation angle of the molecules in the magnetic field, (vii) determining Saupe order matrix elements for the domain from the atomic coordinates for the domain and the axial variations of NMR signals, and (viii) diagonalizing the determined matrix to produce the information on an orientation of the domain;

15. The method according to item 13, wherein the step (b) is a step of (b) providing the information on an orientation of the domain from the atomic coordinates provided previously when the protein was not in contact with the compound;

16. The method according to item 13, wherein in the step (c), the axial variations of NMR signals, which are generated by two-dimensional TROSY NMR spectroscopy and depend on the orientation angle of the molecules in the magnetic field, are variations along a $^{15}N$ axis;

17. The method according to item 16, wherein the Saupe order matrix elements in (iii) are determined by:

with respect to the kth pair of $^{15}N$ nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å determining as $\delta_{ij}$ a tensor value for chemical shift anisotropy of a $^{15}N$ nucleus in an arbitrary residue of the protein, and determining the Saupe order matrix elements $S_{ij}$ defining the molecular orientation with respect to the magnetic field, by contacting the protein with the compound in the presence of the liquid crystalline material, providing $\Delta\delta trosy(k)$ for the kth pair of $^{15}N$ nuclear spins by two-dimensional TROSY NMR spectroscopy, and using the $\Delta\delta trosy(k)$ together with the following equation (1):

$$\Delta\delta trosy(k)=\Sigma S_{ij}\{0.5 D^0_{nh}\cos\phi^k_i\cos\phi^k_j+(\tfrac{2}{3})\delta_{ij}\} \qquad (1)$$

i, j=x, y, z;

18. The method according to item 14, wherein in the step (b), the axial variations of NMR signals, which are generated by two-dimensional TROSY NMR spectroscopy and depend on the orientation angle of the molecules in the magnetic field, are variations along a $^{15}N$ axis;

19. The method according to item 18, wherein the Saupe order matrix elements in (vii) are determined by:

with respect to the kth pair of $^{15}N$ nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å determining as $\delta_{ij}$ a tensor value for chemical shift anisotropy of a $^{15}N$ nucleus in an arbitrary residue of the protein, and determining the Saupe order matrix elements $S_{ij}$ defining the molecular orientation with respect to the magnetic field, by making no contact of the protein with the compound in the presence of the liquid crystalline material, providing $\Delta\delta$trosy (k) for the kth pair of $^{15}N$ nuclear spins of the protein by two-dimensional TROSY NMR spectroscopy, and using the $\Delta\delta$trosy(k) together with the following equation (1):

$$\Delta\delta\text{trosy}(k) = \Sigma S_{ij}\{0.5 D^0_{nh} \cos\phi^k_i \cos\phi^k_j + (2/3)\delta_{ij}\} \quad (1)$$

i, j=x, y, z;

20. The method according to item 17 or 19, wherein the comparison with respect to the information on an orientation in the step (c) is carried out by:

(ix) providing directions of orientation tensor axes by a first three unit vectors perpendicular to each other, by using the information on an orientation of the domain in the protein before the protein is contacted with the compound, wherein the first three unit vectors are expressed by $$\vec{e}_{fx}, \quad \vec{e}_{fy}, \quad \vec{e}_{fz}$$

(x) providing directions of orientation tensor axes by a second three unit vectors perpendicular to each other, by using the information on an orientation of the domain in the protein after the protein is contacted with the compound, wherein the second three unit vectors are expressed by $$\vec{e}_{bx}, \quad \vec{e}_{by}, \quad \vec{e}_{bz}$$

(xi) denoting respective angles between the individual first unit vectors and the individual second unit vectors by a, b and c, (xii) giving a degree of orientational change by the following equation:

$$\text{degree of orientational change} = a^2 + b^2 + c^2$$

wherein the degree of orientational change is compared;

21. The method according to item 14, further comprising a step of identifying a position on the protein to which the compound is bound;

22. The method according to item 21, wherein the step of identifying a position on the protein to which the compound is bound is carried out by comparing the two-dimensional TROSY NMR spectrum obtained in the step (b) with the two-dimensional TROSY NMR spectrum obtained in the step (c) to detect a spectral change, and identifying an amino acid residue which has induced the spectral change;

23. The method according to item 13, wherein the liquid crystalline material comprises a mixture selected from the group consisting of:

a mixture of dimyristoylphosphatidylcholine (DMPC) and dihexanoylphosphatidylcholine (DHPC), a mixture of dimyristoylphosphatidylcholine (DMPC), dihexanoylphosphatidylcholine (DHPC), and sodium dodecyl sulfate (SDS), a mixture of dimyristoylphosphatidylcholine (DMPC), dihexanoylphosphatidylcholine (DHPC), and cetyltrimethylammonium bromide (CTAB), a mixture of 1,2-di-O-dodecyl-sn-glycero-3-phosphocholine (DIODPC) and 3-(cholamidepropyl)-dimethylammonio-2-hydroxy-1-propane sulfate (CHAPS), a mixture of n-alkyl-poly(ethyleneglycol)/n-alkylalcohol, filamentous phage, a mixture of cetylpyridinium chloride (CPCl)-hexanol-NaCl, a mixture of cetylpyridinium bromide (CPBr)-hexanol-NaCl, a purple membrane fragment of *Halobacterium* spp., microcrystalline cellulose, and polyacrylamide gel;

24. The method according to item 23, wherein the liquid crystalline material is the mixture of 7.5% (w/v) composed of dimyristoylphosphatidylcholine (DMPC), dihexanoylphosphatidylcholine (DHPC), and cetyltrimethylammonium bromide (CTAB);

25. A method of selecting a second compound capable of inducing a structural change in a protein on contact with the protein, which is similar to a structural change in the protein induced by a first compound on contact with the protein, comprising the steps of:

(a) selecting a domain in the protein;

(b) providing information on an orientation of the domain when the protein is in contact with the first compound;

(c) providing information on an orientation of the domain when the protein is in contact with the second compound, by (i) providing known atomic coordinates for the domain, (ii) providing axial variations of NMR signals, which are generated from the protein in contact with the second compound in the presence of a liquid crystalline material by two-dimensional TROSY NMR spectroscopy and depend on an orientation angle of the molecules in a magnetic field, (iii) determining Saupe order matrix elements for the domain from the atomic coordinates for the domain and the axial variations of NMR signals, and (iv) diagonalizing the determined matrix to produce the information on an orientation of the domain;

(d) making a comparison between the information on an orientation provided in step (b) and the information on an orientation provided in step (c); and (e) determining from the results obtained by the comparison in step (d) if the structural change in the protein induced by the second compound on contact with the protein is similar to the structural change in the protein induced by the first compound on contact with the protein;

26. The method according to item 25, wherein the step (b) is a step of:

(b) providing the information on an orientation of the domain when the protein is in contact with the first compound, by (v) providing known atomic coordinates for the domain, (vi) providing axial variations of NMR signals, which are generated from the protein in contact with the first compound in the presence of the liquid crystalline material by two-dimensional TROSY NMR spectroscopy and depend on an orientation angle of the molecules in the magnetic field, (vii) determining Saupe order matrix elements for the domain from the atomic coordinates for the domain and the axial variations of NMR signals, and (viii) diagonalizing the determined matrix to produce the information on an orientation of the domain;

27. The method according to item 25, wherein the step (b) is a step of (b) providing the information on an orientation of the domain from the atomic coordinates provided previously when the protein was in contact with the first compound;

28. The method according to item 25, wherein in the step (c), the axial variations of NMR signals, which are generated by two-dimensional TROSY NMR spectroscopy and depend on the orientation angle of the molecules in the magnetic field, are variations along a $^{15}$N axis;

29. The method according to item 28, wherein the Saupe order matrix elements in (iii) are determined by:

with respect to the kth pair of $^{15}$N nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å, determining as $\delta_{ij}$ a tensor value for chemical shift anisotropy of a $^{15}$N nucleus in an arbitrary residue of the protein, and determining the Saupe order matrix elements $S_{ij}$ defining the molecular orientation with respect to the magnetic field, by contacting the protein with the compound in the presence of the liquid crystalline material, providing $\Delta\delta$trosy(k) for the kth pair of $^{15}$N nuclear spins of the protein by two-dimensional TROSY NMR spectroscopy, and using the $\Delta\delta$trosy(k) together with the following equation (1):

$$\Delta\delta\text{trosy}(k)=\Sigma S_{ij}\{0.5D^0_{nh}\cos\phi^k_i\cos\phi^k_j+(2/3)\delta_{ij}\} \qquad (1)$$

i, j=x, y, z;

30. The method according to item 26, wherein in the step (b), the axial variations of NMR signals, which are generated by two-dimensional TROSY NMR spectroscopy and depend on the orientation angle of the molecules in the magnetic field, are variations along a $^{15}$N axis;

31. The method according to item 30, wherein the Saupe order matrix elements in (vii) are determined by:

with respect to the kth pair of $^{15}$N nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å, determining as $\delta_{ij}$ a tensor value for chemical shift anisotropy of a $^{15}$N nucleus in an arbitrary residue of the protein, and determining the Saupe order matrix elements $S_{ij}$ defining the molecular orientation with respect to the magnetic field, by contacting the protein with the second compound in the presence of the liquid crystalline material, providing $\Delta\delta$trosy (k) for the kth pair of $^{15}$N nuclear spins of the protein by two-dimensional TROSY NMR spectroscopy, and using the $\Delta\delta$trosy(k) together with the following equation (1):

$$\Delta\delta\text{trosy}(k)=\Sigma S_{ij}\{0.5D^0_{nh}\cos\phi^k_i\cos\phi^k_j+(2/3)\delta_{ij}\} \qquad (1)$$

i, j=x, y, z;

32. The method according to item 29 or 31, wherein the comparison with respect to the information on an orientation in the step (d) is carried out by:

(ix) providing directions of orientation tensor axes by a first three unit vectors perpendicular to each other, by using the information on an orientation of the domain in the protein when the protein is contacted with the first compound, wherein the first three unit vectors are expressed by $$\overrightarrow{e_{ax}}, \quad \overrightarrow{e_{ay}}, \quad \overrightarrow{e_{az}}$$

(x) providing directions of orientation tensor axes by a second three unit vectors perpendicular to each other, by using the information on an orientation of the domain in the protein when the protein is contacted with the second compound, wherein the second three unit vectors are expressed by $$\overrightarrow{e_{bx}}, \quad \overrightarrow{e_{by}}, \quad \overrightarrow{e_{bz}}$$

(xi) denoting respective angles between the individual first unit vectors and the individual second unit vectors by a, b and c and using the a, b and c as indices for the comparison with respect to the information on an orientation;

33. The method according to item 29 or 31, wherein the comparison with respect to the information on an orientation in the step (d) is carried out by:

(ix) providing directions of orientation tensor axes by a first three unit vectors perpendicular to each other, by using the information on an orientation of the domain in the protein when the protein is contacted with the first compound, wherein the first three unit vectors are expressed by $$\overrightarrow{e_{ax}}, \quad \overrightarrow{e_{ay}}, \quad \overrightarrow{e_{az}}$$

(x) providing directions of orientation tensor axes by a second three unit vectors perpendicular to each other, by using the information on an orientation of the domain in the protein when the protein is contacted with the second compound, wherein the second three unit vectors are expressed by $$\overrightarrow{e_{bx}}, \quad \overrightarrow{e_{by}}, \quad \overrightarrow{e_{bz}}$$

(xi) denoting respective angles between the individual first unit vectors and the individual second unit vectors by a, b and c, and (xii) giving a degree of orientational similarity to the active conformation by the following equation:

$$\text{degree of orientational similarity to the active conformation}=a^2+b^2+c^2$$

wherein the degree of orientational similarity to the active conformation is used as index for the comparison with respect to the information on an orientation;

34. The method according to item 25, further comprising the step of identifying a position on the protein to which at least one of the first and second compounds is bound;

35. The method according to item 34, wherein the step of identifying a position on the protein to which at least one of the first and second compounds is bound is carried out by comparing a two-dimensional TROSY NMR spectrum obtained in the absence of the compound with a two-dimensional TROSY NMR spectrum obtained in the presence of the compound to detect a spectral change, and identifying an amino acid residue which has induced the spectral change;

36. The method according to item 25, wherein the liquid crystalline material comprises a mixture selected from the group consisting of:
a mixture of dimyristoylphosphatidylcholine (DMPC) and dihexanoylphosphatidylcholine (DHPC),
a mixture of dimyristoylphosphatidylcholine (DMPC), dihexanoylphosphatidylcholine (DHPC), and sodium dodecyl sulfate (SDS),
a mixture of dimyristoylphosphatidylcholine (DMPC), dihexanoylphosphatidylcholine (DHPC), and cetyltrimethylammonium bromide (CTAB),
a mixture of 1,2-di-O-dodecyl-sn-glycero-3-phosphocholine (DIODPC) and 3-(cholamidepropyl)-dimethylammonio-2-hydroxy-1-propane sulfate (CHAPS),
a mixture of n-alkyl-poly(ethyleneglycol)/n-alkylalcohol,
filamentous phage,
a mixture of cetylpyridinium chloride (CPCl)-hexanol-NaCl,
a mixture of cetylpyridinium bromide (CPBr)-hexanol-NaCl,
a purple membrane fragment of *Halobacterium* spp.,
microcrystalline cellulose, and
polyacrylamide gel;

37. The method according to item 36 wherein the liquid crystalline material is the mixture of 7.5% (w/v) composed of dimyristoylphosphatidylcholine (DMPC), dihexanoylphosphatidylcholine (DHPC), and cetyltrimethylammonium bromide (CTAB);

38. A program of digitizing a structural change in a selected domain within a protein when the protein is contacted with a compound, comprising carrying out on a computer the means for:

(a) providing information on an orientation of the domain when the protein is not in contact with the compound;

(b) providing information on an orientation of the domain when the protein is in contact with the compound, by (i) providing data on known atomic coordinates for the domain, (ii) providing data on axial variations of NMR signals, which are generated from the protein in contact with the compound in the presence of a liquid crystalline material by two-dimensional TROSY NMR spectroscopy and depend on an orientation angle of the molecules in a magnetic field, (iii) determining Saupe order matrix elements for the domain from the atomic coordinates for the domain and the axial variations of NMR signals, and (iv) diagonalizing the determined matrix to produce the information on an orientation of the domain; and (c) calculating the structural change in the protein by a difference between the information on an orientation provided in means (a) and the information on an orientation provided in means (b);

39. The program according to item 38, wherein the means (a) is means for (a) providing information on an orientation of the domain when the protein is not in contact with the compound, by (v) providing the known atomic coordinates for the domain, (vi) providing axial variations of NMR signals, which are generated from the protein in no contact with the compound in the presence of the liquid crystalline material by two-dimensional TROSY NMR spectroscopy and depend on an orientation angle of the molecules in the magnetic field, (vii) determining Saupe order matrix elements for the domain from the atomic coordinates for the domain and the axial variations of NMR signals, and (viii) diagonalizing the determined matrix to produce the information on an orientation of the domain;

40. The program according to item 38, wherein the means (a) is means for (a) providing the information on an orientation of the domain from the atomic coordinates provided previously when the protein was not in contact with the compound;

41. The program according to item 38, wherein in the step (b), the axial variations of NMR signals, which are generated by two-dimensional TROSY NMR spectroscopy and depend on the orientation angle of the molecules in the magnetic field, are variations along a $^{15}$N axis;

42. The program according to item 41, wherein the Saupe order matrix elements in (iii) are determined by:
with respect to the kth pair of $^{15}$N nuclear spins in the domain,
providing $\phi^k_i$ as a vector angle of an N—H bond having the kth pair of spins in the domain to the ith molecular axis,
providing $\phi^k_j$ as a vector angle of an N—H bond having the kth pair of spins in the domain to the jth molecular axis,
setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å,
determining as $\delta_{ij}$ a tensor value for chemical shift anisotropy of a $^{15}$N nucleus in an arbitrary residue of the protein, and
determining the Saupe order matrix elements $S_{ij}$ defining the molecular orientation with respect to the magnetic field, by contacting the protein with the compound in the presence of the liquid crystalline material, providing $\Delta\delta$trosy(k) for the kth pair of $^{15}$N nuclear spins of the protein by two-dimensional TROSY NMR spectroscopy, and using the $\Delta\delta$trosy(k) together with the following equation (1):

$$\Delta\delta\text{trosy}(k) = \Sigma S_{ij}\{0.5 D^0_{nh} \cos\phi^k_i \cos\phi^k_j + (2/3)\delta_{ij}\} \quad (1)$$

i, j=x, y, z;

43. The program according to item 39, wherein in the step (a), the axial variations of NMR signals, which are generated by two-dimensional TROSY NMR spectroscopy and depend on the orientation angle of the molecules in the magnetic field, are variations along a $^{15}$N axis;

44. The program according to item 43, wherein the Saupe order matrix elements in (vii) are determined by:
with respect to the kth pair of $^{15}$N nuclear spins in the domain,
providing $\phi^k_i$ as a vector angle of an N—H bond having the kth pair of spins in the domain to the ith molecular axis,
providing $\phi^k_j$ as a vector angle of an N—H bond having the kth pair of spins in the domain to the jth molecular axis,
setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å,
determining as $\delta_{ij}$ a tensor value for chemical shift anisotropy of a $^{15}$N nucleus in an arbitrary residue of the protein, and determining the Saupe order matrix elements $S_{ij}$ defining the molecular orientation with respect to the magnetic field, by making no contact of the protein with the compound in the presence of the liquid crystalline material, providing $\Delta\delta$trosy (k) for the kth pair of $^{15}$N nuclear spins of the protein by two-dimensional TROSY NMR spectroscopy, and using the $\Delta\delta$trosy(k) together with the following equation (1):

$$\Delta\delta\text{trosy}(k) = \Sigma S_{ij}\{0.5 D^0{}_{nh} \cos\phi^k{}_i \cos\phi^k{}_j + (2/3)\delta_{ij}\} \quad (1)$$

i, j=x, y, z;

45. The program according to item 42 or 44, wherein a structural change in the protein when the protein and the compound are contacted is digitized as degree of orientational change by:

(ix) providing directions of orientation tensor axes by a first three unit vectors perpendicular to each other, by using the information on an orientation of the domain in the protein before the protein is contacted with the compound, wherein the first three unit vectors are expressed by $$\vec{e}_{fx}, \quad \vec{e}_{fy}, \quad \vec{e}_{fz}$$

(x) providing directions of orientation tensor axes by a second three unit vectors perpendicular to each other, by using the information on an orientation of the domain in the protein after the protein is contacted with the compound, wherein the second three unit vectors are expressed by $$\vec{e}_{bx}, \quad \vec{e}_{by}, \quad \vec{e}_{bz}$$

(xi) denoting respective angles between the individual first unit vectors and the individual second unit vectors by a, b and c, (xii) giving a degree of orientational change by the following equation:

degree of orientational change=$a^2+b^2+c^2$;

46. The program according to item 39, further comprising means for identifying a position on the protein to which the compound is bound;

47. The program according to item 46, wherein the means of identifying a position on the protein to which the compound is bound is carried out by comparing the two-dimensional TROSY NMR spectrum obtained in the step (a) with the two-dimensional TROSY NMR spectrum obtained in the step (b) to detect a spectral change, and identifying an amino acid residue in the protein which has induced the spectral change;

48. A program of selecting a compound capable of inducing a structural change in a domain within a protein when the protein is contacted with the compound, comprising the means of:

(a) providing information on an orientation of the domain when the protein is not in contact with the compound;

(b) providing information on an orientation of the domain when the protein is in contact with the compound, by (i) providing known atomic coordinates for the domain, (ii) providing axial variations of NMR signals, which are generated from the protein in contact with the compound in the presence of a liquid crystalline material by two-dimensional TROSY NMR spectroscopy and depend on an orientation angle of the molecules in a magnetic field, (iii) determining Saupe order matrix elements for the domain from the atomic coordinates for the domain and the axial variations of NMR signals, and (iv) diagonalizing the determined matrix to produce the information on an orientation of the domain; and (c) determining if the compound is capable of inducing a structural change in the domain when the protein is contacted with the compound, by making a comparison between the information on an orientation provided in step (a) and the information on an orientation provided in step (b);

49. The program according to item 48, wherein the means (a) is means for (a) providing information on an orientation of the domain when the protein is not in contact with the compound, by (v) providing the known atomic coordinates for the domain, (vi) providing axial variations of NMR signals, which are generated from the protein in no contact with the compound in the presence of the liquid crystalline material by two-dimensional TROSY NMR spectroscopy and depend on an orientation angle of the molecules in the magnetic field, (vii) determining Saupe order matrix elements for the domain from the atomic coordinates for the domain and the axial variations of NMR signals, and (viii) diagonalizing the determined matrix to produce the information on an orientation of the domain;

50. The program according to item 48, wherein the means (a) is means for (a) providing the information on an orientation of the domain from the atomic coordinates provided previously when the protein was not in contact with the compound;

51. The program according to item 48, wherein in the step (b), the axial variations of NMR signals, which are generated by two-dimensional TROSY NMR spectroscopy and depend on the orientation angle of the molecules in the magnetic field, are variations along a $^{15}$N axis;

52. The program according to item 51, wherein the Saupe order matrix elements in (iii) are determined by:

with respect to the kth pair of $^{15}$N nuclear spins in the domain, providing $\phi^k{}_i$ as a vector angle of an N—H bond having the kth pair of spins in the domain to the ith molecular axis, providing $\phi^k{}_j$ as a vector angle of an N—H bond having the kth pair of spins in the domain to the jth molecular axis, setting a static dipolar coupling $D^0{}_{nh}$ at 23.0 kHz for a length of the N—H bond of 1.02 Å, or setting a static dipolar coupling $D^0{}_{nh}$ at 21.7 kHz for a length of the N—H bond of 1.04 Å, determining as $\delta_{ij}$ a tensor value for chemical shift anisotropy of a $^{15}$N nucleus in an arbitrary residue of the protein, and determining the Saupe order matrix elements $S_{ij}$ defining the molecular orientation with respect to the magnetic field, by contacting the protein with the compound in the presence of the liquid crystalline material, providing $\Delta\delta$trosy(k) for the kth pair of $^{15}$N nuclear spins of the protein by two-dimensional TROSY NMR spectroscopy, and using the $\Delta\delta$trosy(k) together with the following equation (1):

$$\Delta\delta\text{trosy}(k) = \Sigma S_{ij}\{0.5 D^0{}_{nh} \cos\phi^k{}_i \cos\phi^k{}_j + (2/3)\delta_{ij}\} \quad (1)$$

i, j=x, y, z;

53. The program according to item 52, wherein in the step (a), the axial variations of NMR signals, which are generated by two-dimensional TROSY NMR spectroscopy and depend on the orientation angle of the molecules in the magnetic field, are variations along a $^{15}$N axis;

54. The program according to item 53, wherein the Saupe order matrix elements in (vii) are determined by:

with respect to the kth pair of $^{15}$N nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å, determining as $\delta_{ij}$ a tensor value for chemical shift anisotropy of a $^{15}$N nucleus in an arbitrary residue of the protein, and determining the Saupe order matrix elements $S_{ij}$ defining the molecular orientation with respect to the magnetic field, by making no contact of the protein with the compound in the presence of the liquid crystalline material, providing $\Delta\delta$trosy(k) for the kth pair of $^{15}$N nuclear spins of the protein by two-dimensional TROSY NMR spectroscopy, and using the $\Delta\delta$trosy(k) together with the following equation (1):

$$\Delta\delta\text{trosy}(k)=\Sigma S_{ij}\{0.5D^0_{nh}\cos\phi^k_i\cos\phi^k_j+(2/3)\delta_{ij}\} \quad (1)$$

i, j=x, y, z;

55. The program according to item 52 or 54, wherein the comparison with respect to the information on an orientation in the step (c) is carried out by:

(ix) providing directions of orientation tensor axes by a first three unit vectors perpendicular to each other, by using the information on an orientation of the domain in the protein before the protein is contacted with the compound, wherein the first three unit vectors are expressed by $$\vec{e}_{fx}, \quad \vec{e}_{fy}, \quad \vec{e}_{fz}$$

(x) providing directions of orientation tensor axes by a second three unit vectors perpendicular to each other, by using the information on an orientation of the domain in the protein after the protein is contacted with the compound, wherein the second three unit vectors are expressed by $$\vec{e}_{bx}, \quad \vec{e}_{by}, \quad \vec{e}_{bz}$$

(xi) denoting respective angles between the individual first unit vectors and the individual second unit vectors by a, b and c, (xii) giving a degree of orientational change by the following equation:

degree of orientational change=$a^2+b^2+c^2$ wherein the degree of orientational change is compared;

56. The program according to item 48, further comprising means for identifying a position on the protein to which the compound is bound;

57. The program according to item 56, wherein the means of identifying a position on the protein to which the compound is bound is carried out by comparing the two-dimensional TROSY NMR spectrum obtained in the step (a) with the two-dimensional TROSY NMR spectrum obtained in the step (b) to detect a spectral change, and identifying an amino acid residue in the protein which has induced the spectral change;

58. A program of selecting a second compound capable of inducing a structural change in a domain within a protein on contact with the protein, which is similar to a structural change in the domain within the protein induced by a first compound on contact with the protein, comprising the means of:

(a) providing information on an orientation of the domain when the protein is in contact with the first compound;

(b) providing information on an orientation of the domain when the protein is in contact with the second compound, by (i) providing known atomic coordinates for the domain, (ii) providing axial variations of NMR signals, which are generated from the protein in contact with the second compound in the presence of a liquid crystalline material by two-dimensional TROSY NMR spectroscopy and depend on an orientation angle of the molecules in a magnetic field, (iii) determining Saupe order matrix elements for the domain from the atomic coordinates for the domain and the axial variations of NMR signals, and (iv) diagonalizing the determined matrix to produce the information on an orientation of the domain;

(c) making a comparison between the information on an orientation provided in means (a) and the information on an orientation provided in means (b); and (d) determining from the results obtained by the comparison in means (c) if the structural change in the protein induced by the second compound on contact with the protein is similar to the structural change in the protein induced by the first compound on contact with the protein;

59. The program according to item 25, wherein the means (a) is means of:

(a) providing the information on an orientation of the domain when the protein is in contact with the first compound, by (v) providing known atomic coordinates for the domain, (vi) providing axial variations of NMR signals, which are generated from the protein in contact with the first compound in the presence of the liquid crystalline material by two-dimensional TROSY NMR spectroscopy and depend on an orientation angle of the molecules in the magnetic field, (vii) determining Saupe order matrix elements for the domain from the atomic coordinates for the domain and the axial variations of NMR signals, and (viii) diagonalizing the determined matrix to produce the information on an orientation of the domain;

60. The program according to item 58, wherein the means (a) is means of (a) providing the information on an orientation of the domain from the atomic coordinates provided previously when the protein was in contact with the first compound;

61. The program according to item 58, wherein in the step (b), the axial variations of NMR signals, which are generated by two-dimensional TROSY NMR spectroscopy and depend on the orientation angle of the molecules in the magnetic field, are variations along a $^{15}$N axis;

62. The program according to item 61, wherein the Saupe order matrix elements in (iii) are determined by:

with respect to the kth pair of $^{15}$N nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å, determining as $\delta_{ij}$ a tensor value for chemical shift anisotropy of a $^{15}$N nucleus in an arbitrary residue of the protein, and determining the Saupe order matrix elements $S_{ij}$ defining the molecular orientation with respect to the magnetic field, by contacting the protein with the compound in the presence of the liquid crystalline material, providing $\Delta\delta\text{trosy}(k)$ for the kth pair of $^{15}$N nuclear spins of the protein by two-dimensional TROSY NMR spectroscopy, and using the $\Delta\delta\text{trosy}(k)$ together with the following equation (1):

$$\Delta\delta\text{trosy}(k)=\Sigma S_{ij}\{0.5D^0_{nh}\cos\phi^k_i\cos\phi^k_j+(\tfrac{2}{3})\delta_{ij}\} \quad (1)$$

i, j=x, y, z;

63. The program according to item 59, wherein in the step (a), the axial variations of NMR signals, which are generated by two-dimensional TROSY NMR spectroscopy and depend on the orientation angle of the molecules in the magnetic field, are variations along a $^{15}$N axis;

64. The program according to item 63, wherein the Saupe order matrix elements in (vii) are determined by:

with respect to the kth pair of $^{15}$N nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å, determining as $\delta_{ij}$ a tensor value for chemical shift anisotropy of a $^{15}$N nucleus in an arbitrary residue of the protein, and determining the Saupe order matrix elements $S_{ij}$ defining the molecular orientation with respect to the magnetic field, by contacting the protein with the second compound in the presence of the liquid crystalline material, providing $\Delta\delta\text{trosy}(k)$ for the kth pair of $^{15}$N nuclear spins of the protein by two-dimensional TROSY NMR spectroscopy, and using the $\Delta\delta\text{trosy}(k)$ together with the following equation (1):

$$\Delta\delta\text{trosy}(k)=\Sigma S_{ij}\{0.5D^0_{nh}\cos\phi^k_i\cos\phi^k_j+(\tfrac{2}{3})\delta_{ij}\} \quad (1)$$

i, j=x, y, z;

65. The program according to item 62 or 64, wherein the comparison with respect to the information on an orientation in the step (c) is carried out by:

(ix) providing directions of orientation tensor axes by a first three unit vectors perpendicular to each other, by using the information on an orientation of the domain in the protein when the protein is contacted with the first compound, wherein the first three unit vectors are expressed by $$\vec{e}_{ax}, \vec{e}_{ay}, \vec{e}_{az}$$

(x) providing directions of orientation tensor axes by a second three unit vectors perpendicular to each other, by using the information on an orientation of the domain in the protein when the protein is contacted with the second compound, wherein the second three unit vectors are expressed by $$\vec{e}_{bx}, \vec{e}_{by}, \vec{e}_{bz}$$

(xi) denoting respective angles between the individual first unit vectors and the individual second unit vectors by a, b and c and using the a, b and c as indices for the comparison with respect to the information on an orientation;

66. The program according to item 62 or 64, wherein the comparison with respect to the information on an orientation in the step (c) is carried out by:

(ix) providing directions of orientation tensor axes by a first three unit vectors perpendicular to each other, by using the information on an orientation of the domain in the protein when the protein is contacted with the first compound, wherein the first three unit vectors are expressed by $$\vec{e}_{ax}, \vec{e}_{ay}, \vec{e}_{az}$$

(x) providing directions of orientation tensor axes by a second three unit vectors perpendicular to each other, by using the information on an orientation of the domain in the protein when the protein is contacted with the second compound, wherein the second three unit vectors are expressed by $$\vec{e}_{bx}, \vec{e}_{by}, \vec{e}_{bz}$$

(xi) denoting respective angles between the individual first unit vectors and the individual second unit vectors by a, b and c, and (xii) giving a degree of orientational similarity to the active conformation by the following equation:

$$\text{degree of orientational similarity to the active conformation}=a^2+b^2+c^2$$

wherein the degree of orientational similarity to the active conformation is used as index for the comparison with respect to the information on an orientation;

67. The program according to item 58, further comprising the means of identifying a position on the protein to which at least one of the first and second compounds is bound;

68. The program according to item 67, wherein the means of identifying a position on the protein to which at least one of the first and second compounds is bound is carried out by comparing a two-dimensional TROSY NMR spectrum obtained in the absence of the compound with a two-dimensional TROSY NMR spectrum obtained in the presence of the compound to detect a spectral change, and identifying an amino acid residue which has induced the spectral change;

69. An apparatus capable of carrying out the method according to item 1, 13 or 25;

70. An apparatus provided with the program according to item 38, 48 or 58; and

71. A storage medium containing the program according to item 38, 48 or 58.

Advantages of the Invention

The present invention provides a method of estimating a conformational change in a target protein, which is induced by addition of a compound into a solution of the target protein, by a change thereof in a TROSY correlation NMR spectrum (for example, $^1$H/$^{15}$N NMR spectrum) and a program therefor. The present invention provides a novel method capable of concurrent observation of 1) a site on a target protein to which a compound is bound, and 2) a structural change in the target protein induced by the compound.

BEST MODE FOR CARRYING OUT THE INVENTION

Figure 1:
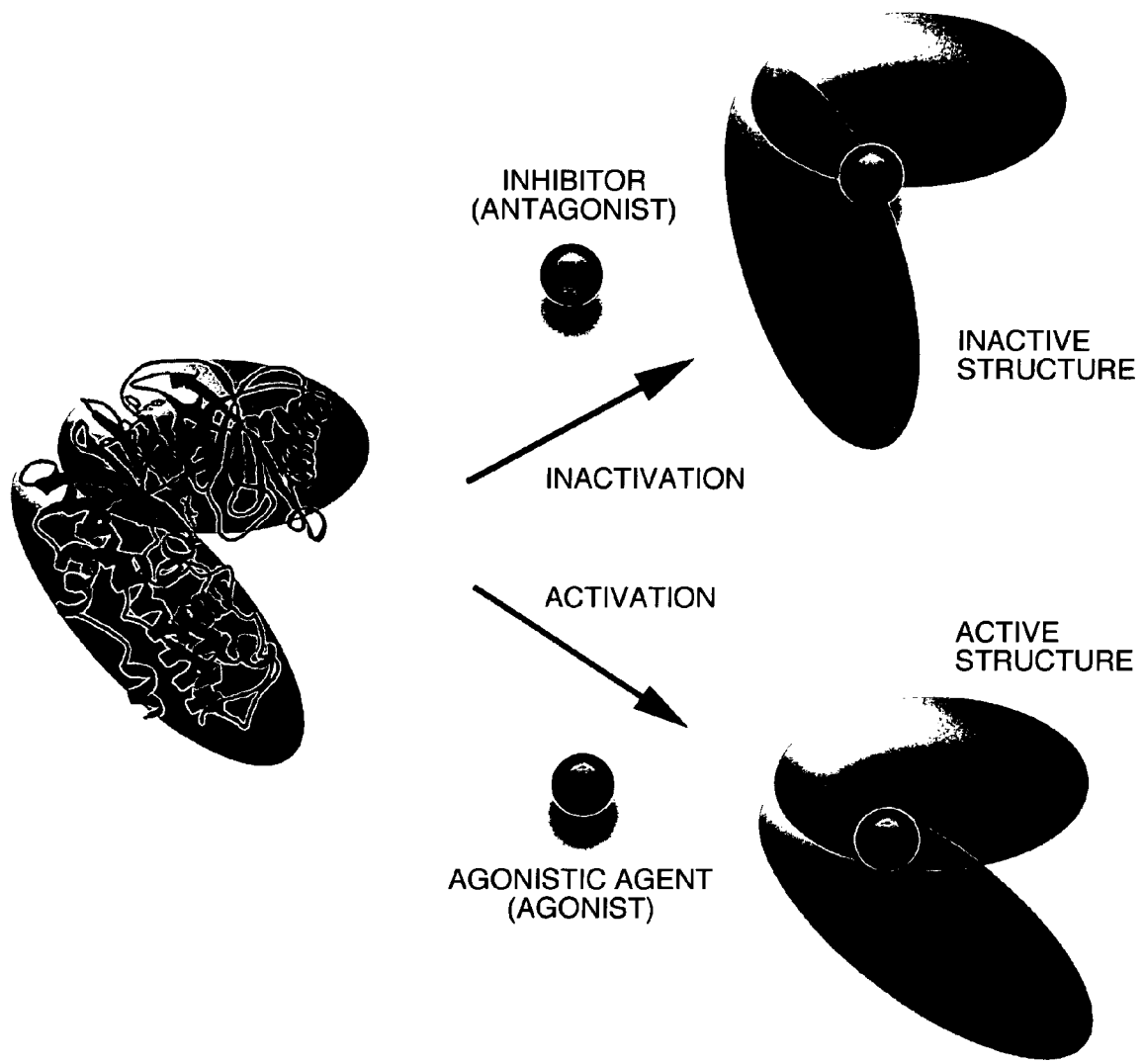
FIG. 1 illustrates a method of selectively identifying an agonistic lead compound based on a relative orientational change between domains.

Hereinbelow the present invention is described. It should be noted that all through this specification, expression as a singular form includes the concept of the plural referent unless otherwise stated. Therefore, as for the articles for a singular form (for example, "a", "an", "the", etc. in the case of English), it should be understood that they include concept of the plural referent unless otherwise stated. In addition, it should be understood that all terms used in this specification are used with a meaning usually used in the art unless otherwise stated. Accordingly, all technical and scientific terms used herein have the same meaning as commonly understood by those skilled in the art to which this invention belongs unless defined otherwise. When they contradict each other, this specification (including definitions) takes priority.

(Definition of Terms)

The definitions of the terms used in this specification in particular are listed below.

The terms "protein", "polypeptide", "oligopeptide" and "peptide" used in this specification are used in the same meaning in this specification, and they refer to a polymer of amino acids of any length. The polymer may be linear or branched or may be cyclic. An amino acid may be natural or unnatural or may be a modified amino acid. As for these terms, they can also be assembled into a complex of plural polypeptide chains. These terms also encompass a natural or artificially modified amino acid polymer. Such a modification includes, for example, disulfide bond formation, glycosylation, lipidation, acetylation, phosphorylation or any other manipulation or modification (for example, conjugation with a labeling component). This definition also encompasses, for example, a polypeptide containing one or more analogs of amino acids (including, for example, unnatural amino acids), a peptide-like compound (for example, peptoid) and other modifications known in the art.

A "domain" of a protein in this specification means a specific part of a protein molecule including one amino acid residue or at least two consecutive amino acid residues. The domain in this specification may have a specific function or no specific function on its own.

"An amino acid" may be natural or unnatural in this specification. A "derivative amino acid" or "amino acid analog" refers to one which is different from the naturally occurring amino acids but has a function similar to the original amino acid. Such derivative amino acids and amino acid analogs are well-known in the art. The term "natural amino acids" mean L-isomers of natural amino acids. Natural amino acids are glycine, alanine, valine, leucine, isoleucine, serine, methionine, threonine, phenylalanine, tyrosine, tryptophan, cysteine, proline, histidine, asparagic acid, asparagine, glutamic acid, glutamine, γ-carboxy glutamic acid, arginine, ornithine and lysine. All amino acids as used in this specification are of L-type unless indicated otherwise. The term "unnatural amino acid" means an amino acid usually not found naturally in proteins. Examples of unnatural amino acids include norleucine, para-nitrophenylalanine, homophenylalanine, para-fluorophenylalanine, 3-amino-2-benzylpropionic acid, D-or L-type of homoarginine and D-phenylalanine. An "amino acid analog" refers to a molecule which is not an amino acid but similar to an amino acid in physical properties and/or function. Examples of amino acid analogs include ethionine, canavanine, 2-methylglutamine. An amino acid mimic refers to a compound which has a structure different from the general chemical structure of an amino acid but functions in a manner similar to a naturally occurring amino acid.

An amino acid can be mentioned in this specification either by a publicly known three-letter code thereof or by a one-letter code recommended by IUPAC-IUB Biochemical Nomenclature Commission. A nucleotide can be mentioned likewise by a commonly accepted one-letter code.

In this specification, an "equivalent" amino acid refers to an amino acid which has or is expected to have an action similar to a certain amino acid in a protein or polypeptide molecule that is the basis of comparison, and particularly in an enzyme molecule, it refers to an amino acid which exists at a similar place in an active site and has a similar contribution to catalytic activity.

The term "receptor" used in this specification is a biological structure having one or more binding domains which complex with one or more ligands reversibly and specifically, wherein this complex has a biological structure. A receptor may exist completely out of the cell (extracellular receptor), in the cell membrane (provided that parts of the receptor face the environment outside the cell and the cytosol) or completely in the cell (intracellular receptor). They can also function independently of the cell. The receptor in the cell membrane enables the cell to communicate with the space outside the border (for example, signaling) and to function in the transportation of a molecule or ion to the inside and to the outside of the cell. The receptor as used in this specification may be full length of the receptor or a fragment of the receptor.

When a receptor fragment is used, for example, a site related to ligand recognition of receptor protein can be used. The site related to ligand recognition of receptor protein can be identified as follows. The site related to ligand recognition can be estimated from the structure of proteins having high homology or similarity in function by homology and domain search. For example, when calculation is performed with default parameters of BLAST on amino acid sequences of different receptor molecules which bind specifically to the same ligand, a region showing homology of 50% or more, preferably 55% or more, more preferably 60% or more, still more preferably 65% or more is estimated as a ligand recognition site.

Furthermore, those skilled in the art can enable a gene encoding a variant receptor with deletion variation or amino acid substitution introduced to be transiently expressed in an animal cell or the like, and easily determine the region which is essential to the function.

The term "ligand" used in this specification is a binding partner to a specific receptor or a family of receptors. The ligand may be an endogenous ligand to the receptor or alternatively it can be a synthetic ligand to the receptor such as a drug, drug candidate or pharmacological means.

An "agonist" in this specification refers to a factor which binds to a receptor for a certain biologically active substance (ligand) and develops an effect identical to (or similar to) the effect of the substance.

An "antagonist" in this specification refers to a factor which competes against a certain biologically active substance (ligand) for binding itself to the receptor but develops no physiological effect of itself through the receptor. The antagonist also encompasses a reversal agent, a blocking agent (blocker), an inhibitory agent (inhibitor), etc.

"NMR" in this specification means magnetic nuclear resonance. When a population of nuclei having magnetic moments is placed in a static magnetic field $B_0$, the nuclei are distributed at discontinuous energy levels according to the magnitude of the magnetic moment and the strength of the magnetic field by nuclear Zeeman effect. The phenomenon of resonance absorption observed when an electromagnetic radiation having a frequency equivalent to a difference between these levels is exposed is referred to as magnetic nuclear resonance.

"Two-dimensional NMR" in this specification refers to a method to develop a nuclear magnetic resonance spectrum in two frequency axes. Different pulses are used in this measurement and Fourier transformation is performed using the time interval of the pulses and the time after the observation pulse as two time axes. Signal intensity is usually expressed by contour. Typically, two-dimensional NMR includes TROSY (transverse relaxation-optimized spectroscopy), COSY (two dimensional shift correlation MNR method), SECSY (two dimensional spin echo correlation spectroscopy), FOCSY (two dimensional foldover-corrected spectroscopy), HOHAHA (two dimensional homonuclear Hartmann-Hahn spectroscopy), NOESY (two dimensional NOE spectroscopy), 2D-J technique (two-dimensional J-resolved spectroscopy) and relayed COSY (relayed coherence transfer spectroscopy) but it is not limited to these. Preferable NMR is TROSY. TROSY is a method which has been developed by Wuthrich et al. and suitable for super-high magnetic field NMR (Proc. Natl. Acad. Sci. USA vol. 94, pp. 12366-12371 (1997)). In NMR of a molecule having a high molecular weight, nuclear magnetic relaxation is governed by (1) magnetic dipolar interaction and (2) chemical shift anisotropy, and the chemical shift anisotropy becomes very large in a super-high magnetic field, which shortens relaxation time and broadens line width. TROSY is a method which lengthens the relaxation time and makes narrower the line width by offsetting these two interactions. TROSY has enabled us to obtain a two-dimensional NMR spectrum for a protein with a high molecular weight (for example, 900 kDa or more).

When two-dimensional NMR is performed in this specification, nuclides of stable isotopes which are used to label the protein include $^{15}N$, $^{13}C$, $^2H$ or a combination thereof but they are not limited to these. Preferable labelings using stable isotope nuclides include $^{15}N$ single labeling, $^{13}C$ single labeling, $^{15}N/^2H$ double labeling, $^{13}C/^2H$ double labeling, and $^{15}N/^{13}C/^2H$ triple labeling.

In this specification, "liquid crystal material" is a material which causes a weak orientation of the target protein. The liquid crystal material includes a mixture of dimyristoylphosphatidylcholine (DMPC) and dihexanoylphosphatidylcholine (DHPC), a mixture of dimyristoylphosphatidylcholine (DMPC) and dihexanoylphosphatidylcholine (DHPC) and sodium dodecyl sulfate (SDS), a mixture of dimyristoylphosphatidylcholine (DMPC) and dihexanoylphosphatidylcholine (DHPC) and cethyltrimethyl ammonium bromide (CTAB), a mixture of 1,2-di-O-dodecyl-sn-glycero-3-phosphocholine (DIODPC) and 3-(cholamidepropyl)-dimethylammonio-2-hydroxy-1-propane sulfate (CHAPS), a mixture of n-alkyl-poly(ethyleneglycol)/n-alkyl alcohol, filamentous phage, a mixture of cetyl pyridinium chloride (CPCl)-hexanol-NaCl a mixture of cetyl pyridinium bromide (CPBr)-hexanol-NaCl, purple membrane fragments of *Halobacterium* genus, microcrystalline cellulose and
polyacrylamide gel, but it is not limited to these.

When the liquid crystal material is a lipid, bicelle made up of the lipid is mixed with the target protein, and the temperature of the mixture is set at phase transition temperature or more, the target protein can be weakly oriented.

The "oriented state of molecule" in this specification is shown by Euler angle which shows tilt of coordinate axis of the molecule from the coordinate axis which assumes static magnetic field direction as Z-axis.

The "information on an orientation" in this specification refers to information about orientation of domain in protein and refers to information obtained as a molecular orientation tensor. For example, in this specification, information on an orientation can be expressed using unit vectors perpendicular to each other.

In this specification, the "axial variations of NMR signals" refers to axial variations dependent on molecular orientation along the frequency axis of two-dimensional NMR developed for a stable isotope element. For example, when $^1H$ is used, they refer to variations dependent on molecular orientation in the direction of $^1H$ axis and when $^{13}C$ is used, they refer to variations dependent on molecular orientation in the direction of $^{13}C$ axis.

For a compound examined in the present invention, any compound can be used, and examples thereof include low molecular organic compounds, low molecular inorganic compounds, nucleic acids, nucleic acid analogs, peptides, peptide analogs, metal ions, but it is not limited to these.

When a low molecular organic compound or a low molecular inorganic compound is synthesized in the present invention, combinatorial chemistry can be used. Combinatorial chemistry is a potent synthesizing process comprising introducing plural substituent groups into a certain basic scaffold by combinatorial technique and synthesizing a certain group of molecules (library) including a number of various compounds in a short period of time and finding out a compound of interest from this molecular group. Various kinds of techniques for combinatorial chemistry are well-known. Historically, the combinatorial chemistry is a technique detonated by development of synthesis technique based on "peptide synthesis" (1963) using beads by Merrifield (U.S.A.) and "split synthetic process" (1991) by Furka (Hungary) and the research and development have been pushed forward energetically since 1992. In particular, the solid phase synthesis is a technique developing rapidly in late years since it matches needs for speedup in that it does not require purification after synthesis.

The terms "polynucleotide", "oligonucleotide" and "nucleic acid" used in this specification are used in the same meaning in this specification, and they refer to a polymer of nucleotides of any length. These terms also encompass a "derivatized oligonucleotide" or "derivatized polynucleotide". The "derivatized oligonucleotide" or "derivatized polynucleotide" refers to an oligonucleotide or a polynucleotide which contains a derivative of nucleotide or a binding between nucleotides different from the ordinary one, and they are used interchangeably. Specific examples of such an oligonucleotide includes 2'-O-methyl-ribonucleotide, derivatized oligonucleotides in which the phosphodiester bond in oligonucleotide is converted into a phosphorothioate bond, derivatized oligonucleotides in which the phosphodiester bond in oligonucleotide is converted into an N3'-P5' phosphoroamidate bond, derivatized oligonucleotides in which the ribose and phosphodiester bond in oligonucleotide is converted into a peptide nucleic acid bond, derivatized oligonucleotides in which uracil in oligonucleotide is replaced by C-5 propynyluracil, derivatized oligonucleotides in which uracil in oligonucleotide is replaced by C-5 thiazole uracil, derivatized oligonucleotides in which cytosine in oligonucleotide is replaced by C-5 propynylcytosine, derivatized oligonucleotides in which cytosine in oligonucleotide is replaced by phenoxazine-modified cytosine, derivatized oligonucleotides in which ribose in DNA is replaced by 2'-O-propylribose and derivatized oligonucleotides in which ribose in oligonucleotide is replaced by 2'-methoxyethoxy ribose. Unless otherwise indicated, a specific nucleic acid sequence is intended to also encompass the explicitly shown sequence as well as conservatively modified variants thereof (for example, degenerate codon substituted sequence) and the complementary sequence. Specifically, the degenerate codon substituted sequence can be attained by making a sequence in which the third position of one or more selected (or all) codons are replaced by a mixed base and/or a deoxyinosine residue (Batzer et al., Nucleic Acid Res. 19:5081 (1991); Ohtsuka et al., J. Biol. Chem. 260: 2605-2608 (1985); Rossolini et al., Mol. Cell. Probes 8:91-98 (1994)). The term "nucleic acid" is also used interchangeably with gene, cDNA, mRNA, oligonucleotide and polynucleotide in this specification. A specific nucleic acid sequence also encompasses "splice variant". Similarly, a specific protein encoded by a nucleic acid tacitly encompasses any protein encoded by the splice variant of the nucleic acid. A "splice variant" is a product of genetic alternative splicing as the name suggests. After transcription, the first nucleic acid transcript can be spliced so that a different (or another) nucleic acid splicing product encodes a different polypeptide. Production mechanism of splice variant varies but includes alternative splicing of exon. This definition also encompasses another polypeptide derived from the same nucleic acid by read-through transcription. This definition encompasses any product of splicing reaction (including a splicing product by recombination).

"Nucleotide" may be natural or unnatural thing in this specification. The "derivatized nucleotide" or "nucleotide analog" refers to one different from naturally occurring nucleotide but having a function similar to the original nucleotide. Such derivatized nucleotide and nucleotide analog are well-known in the art. Examples of such derivatized nucleotide and nucleotide analog include phosphorothioate, phosphoramidate, methyl phosphonate, chiral methyl phosphonate, 2-O-methyl ribonucleotide, peptide-nucleic acid (PNA), but they are not limited to these.

In this specification, a "fragment" refers to a polypeptide or polynucleotide having a sequence length from 1 to n−1 when a full length polypeptide or polynucleotide (length: n) is considered. The length of a fragment can be suitably changed depending on the object and, for example, and, the lower limit of the length includes 3, 4, 5, 6, 7, 8, 9, 10, 15, 20, 25, 30, 40, 50 or more amino acids in the case of polypeptide, and, in addition, length expressed with an integer not specifically listed here (for example, 11) can be appropriate as the lower limit. In addition, in the case of polynucleotide, nucleotides of 5, 6, 7, 8, 9, 10, 15, 20, 25, 30, 40, 50, 75, 100 and more are included, and, in addition, length expressed with an integer not specifically listed here (for example, 11) can be appropriate as the lower limit. When used in this specification, preferably a receptor "fragment" specifically binds to the ligand to which the full length receptor can specifically binds.

The protein used in the present invention may be purified from a natural source of supply or recombinantly expressed by transforming a host cell by means of genetic engineering. The method of genetically engineering a polypeptide includes, for example, a method comprising culturing bacteria which are prokaryote producing the polypeptide and having the recombinant receptor protein accumulated as inclusion body in the bacteria and obtaining the polypeptide by disrupting the host bacteria.

The "transformant" refers to the whole or part of an organism such as a cell created by transforming a host cell. As a transformant, a prokaryotic cell is exemplified. A transformant is also referred to as a transformed cell, transformed tissue, transformed host or the like depending on the target and all of these forms are included in this specification, but it can indicate a specific form in a specific context.

Host bacteria cells to obtain a transformant are not particularly limited as long as they express a polypeptide which maintains bioactivity, and various host bacteria cells conventionally used in gene manipulation can be used. As prokaryotic cells, prokaryotic cells belonging to genus *Escherichia*, genus *Serratia*, genus *Bacillus*, genus *Brevibacterium*, genus *Corynebacterium*, genus *Microbacterium*, genus *Pseudomonas* and the like, for example, *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No, 49, *Escherichia coli* W3110, *Escherichia coli* NY49, *Escherichia coli* BL21(DE3), *Escherichia coli* BL21(DE3)pLysS, *Escherichia coli* HMS174(DE3), *Escherichia coli* HMS174(DE3)pLysS, *Serratia ficaria*, *Serratia fonticola*, *Serratia liquefaciens*, *Serratia marcescens*, *Bacillus subtilis*, *Bacillus amyloliquefaciens*, *Brevibacterium ammmoniagenes*, *Brevibacterium immariophilum* ATCC14068, *Brevibacterium saccharolyticum* ATCC14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, *Pseudomonas* sp. D-0110 can be exemplified.

As for the polypeptide derived from cells obtained according to the present invention, one or more amino acids in the amino acid sequence may be replaced, added and/or deleted and a sugar chain may be replaced, added and/or deleted as long as it has substantially the same effect as a polypeptide of natural type.

A certain amino acid can be replaced by another amino acid in a protein structure for example, on a binding site of a ligand molecule, without apparently decreasing or losing its interactive binding ability. It is the interactive binding ability and property of a protein that determine the biological function of the protein. Therefore, replacement of a specific amino acid in a protein can be performed in an amino acid sequence or at a level of a coding DNA sequence, with the protein still maintaining the original property can be created after the replacement. Therefore, various kinds of modifications can be performed in a peptide or a corresponding DNA encoding this peptide disclosed in this specification without clear loss of biological utility.

When designing modification as mentioned above, hydrophobicity index of amino acids can be taken into consideration. Significance of hydrophobicity index of amino acids for giving interactive biological function in a protein is generally recognized in the art (Kyte J. and Doolittle, R. F., J. Mol. Biol. 157 (1): 105-132, 1982). Hydrophobicity of an amino acid contributes to the secondary structure of the generated protein and subsequently determines the interaction of the protein with other molecules (for example, enzyme, substrate, receptor, DNA, antibody, antigen, etc.). Each amino acid is assigned with a hydrophobicity index based on the hydrophobicity and a property of charge. They are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); triptophan (−0.9); tyrosine (−1.3); proline (−1.6); histidine (−3.2); glutamic acid (−3.5); glutamine (−3.5); asparagic acid (−3.5); asparagine (−3.5); lysine (−3.9); and arginine (−4.5).

It is well-known in the art that another protein still having a similar biological function (for example, a protein which is equivalent in ligand binding capacity) can be produced by replacing a certain amino acid with another amino acid having a similar hydrophobicity index. The hydrophobicity index is preferably within ±2, more preferably within ±1, and still more preferably within ±0.5 in such amino acid replacement. It is understood in the art that such replacement of amino acid based on hydrophobicity is effective. As described in U.S. Pat. No. 4,554,101, the following hydrophilicity indexes are assigned to amino acid residues: arginine (+3.0); lysine (+3.0); asparagic acid (+3.0±1); glutamic acid (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and triptophan (−3.4). It is understood that an amino acid can be replaced with another amino acid having a similar hydrophilicity index and still giving a biological equivalent. The hydrophilicity index is preferably within ±2, more preferably within ±1, and still more preferably within ±0.5 in such an amino acid replacement.

In the present invention, the "conservative replacement" refers to a replacement in which the hydrophilicity index and/or hydrophobicity index resembles as above in the amino acid replacement between the original amino acid and the replaced amino acid. Examples of conservative replacement are well-known to those skilled in the art and, for example, it is replacement in each of the following groups: arginine and lysine; glutamic acid and asparagic acid; serine and threonine; glutamine and asparagine; and valine, leucine and isoleucine but it is not limited to these.

In this specification, the "variant" refers to one partly changed for the original substance such as polypeptide or polynucleotide. Such a variant includes replacement variant, addition variant, deletion variant, trucated variant, allele variant, etc. Alleles refer to genetic variants which belong to the same locus but can be distinguished from each other. Therefore, the "allele variant" refers to a variant having a relation of an allele to a certain gene. A "species homolog or homolog" refers to one which has homology (preferably it is homologous by 60% or more, more preferably it is homologous by 80% or more, 85% or more, 90% or more, or 95% or more) with a certain gene in a species at an amino acid level or a nucleotide level. The method for acquiring such a species homolog is clear from the description of this specification. An "ortholog" is also referred to as orthologous gene and, refers to a gene where two genes derive from the common ancestor through speciation. For example, when hemoglobin gene family having multigene structure is taken as an example, human and mouse α hemoglobin genes are orthologs while human α hemoglobin gene and β hemoglobin gene are paralogs (genes resulted from gene redundancy). Orthologs are useful for estimation of molecule dendrogram and therefore, orthologs can also be useful in the present invention.

A "conservative (modified) variant" is applied to both amino acid sequence and nucleic acid sequence. With regard to a specific nucleic acid sequence, a conservatively modified variant refers to a nucleic acid encoding the same or essentially the same amino acid sequence and when the nucleic acid encodes no amino acid sequence, it refers to essentially the same sequence. Due to degeneracy of genetic code, a plurality of functionally identical nucleic acids encode an arbitrarily appointed protein. For example, all codons GCA, GCC, GCG and GCU encode an amino acid alanine. Therefore, at all positions where alanine is specified by a codon, the codon can be changed to any one of the described corresponding codons without changing the encoded polypeptide. Such a change in nucleic acid is a "silent modification (variation)", one of the conservatively modified variant. All nucleic acid sequences in this specification encoding a polypeptide also describe all possible silent variations of the nucleic acid. It is understood in the art that each codon in nucleic acids (except AUG which is usually the only codon for methionine and TGG which is usually the only codon for tryptophan) can be changed so as to produce functionally the same molecule. Therefore, each silent variation of nucleic acid encoding a polypeptide is tacitly included in each of the described sequence. Preferably such a change can evade replacement of cysteine, an amino acid which has a great influence on higher-order structure of a polypeptide.

In addition to replacement of an amino acid, addition, deletion or modification of an amino acid can be performed so as to make a functionally equivalent polypeptide in this specification. Replacement of an amino acid refers to replacement in which one or more, for example, 1 to 10, preferably 1 to 5, more preferably 1 to 3 amino acids are replaced in the original peptide. Addition of an amino acid refers to addition in which one or more, for example, 1 to 10, preferably 1 to 5, more preferably 1 to 3 amino acids are added to the original peptide. Deletion of an amino acid refers to deletion in which one or more, for example, 1 to 10, preferably 1 to 5, more preferably 1 to 3 amino acids are deleted from the original peptide. Amino acid modification includes amidation, carboxylation, sulfation, halogenation, alkylation, glycosylation, phosphorylation, hydration, acylation (for example, acetylation), but it is not limited to these. A replaced or added amino acid may be a natural amino acid or may be an unnatural amino acid or an amino acid analog. A natural amino acid is preferable.

Such a nucleic acid can be obtained by well-known PCR method and can be also synthesized chemically. These methods may be combined, for example, with site-directed mutagenesis, hybridization method, etc.

In this specification "replacement, addition or deletion" of a polypeptide or polynucleotide refers to replacement, addition or deletion in which an amino acid or a substitute thereof or a nucleotide or a substitute thereof is replaced by, added to or deleted from the original polypeptide or polynucleotide, respectively. Techniques for such replacement, addition or deletion are well-known in the art and examples of such techniques include site-directed mutagenesis technique. Replacement, addition or deletion may be performed in any number not less than one and such a number can be increased as far as the function to be aimed in variant having the replacement, addition or deletion (for example, cancer marker, nerve disease marker) is maintained. For example, such a number can be 1 or several and preferably it can be 20% or less, or 10% or less of the total length, or 100 or less, 50 or less, 25 or less, or the like.

Polymer structures (for example, polypeptide structure) can be described for construction at various levels. As for general discussion on this construction, see for example, Alberts et al., Molecular Biology of the Cell (third edition, 1994) and Cantor and Schimmel, Biophysical Chemistry Part I: The Conformation of Biological Macromolecules (1980). The "primary structure" refers to a specific amino acid sequence of peptides. The "secondary structure" refers to a three-dimensional structure locally positioned in a polypeptide. Generally these structures are well known as domains. A domain is a part of a polypeptide which forms a minute unit of a polypeptide and typically it has a length of 50 to 350 amino acids. Representative domains are made of parts such as $\beta$ sheet ($\beta$ strand) and stretch of $\alpha$-helix. The "tertiary structure" refers to a complete three-dimensional structure of polypeptide monomers. The "quaternary structure" refers to a three-dimensional structure formed by a noncovalent association of independent tertiary units. Terms on anisotropy are used in the same way as the terms known in the field of energy.

The term "biomolecule" used in this specification refers to a molecule related to a living body. The "living body" in this specification refers to a biological organism, and includes animal, plant, fungi, virus, but it is not limited to them. The biomolecule encompasses molecules extracted from the living body, but they are not limited to these and any molecules which can affect the living body are included in the definition of biomolecule. Such a biomolecule includes protein, polypeptide, oligopeptide, peptide, polynucleotide, oligonucleotide, nucleotide, nucleic acid (including, for example, DNA such as cDNA and genome DNA, RNA such as mRNA), polysaccharide, oligosaccharide, lipid, low molecular compound (for example, hormone, ligand, information transmitter, organic low molecular compound, combinatorial library compound), complex molecule thereof, but it is not limited to these. The biomolecule which is preferable in this specification is a receptor, a receptor fragment and a ligand thereof.

When a receptor is used as a protein in this specification, the receptor includes scavenger receptor including lectin-like oxidation LDL receptor (LOX-1), receptor belonging to insulin receptor family, receptor belonging to EGF receptor family, receptor belonging to PDGF receptor family, receptor belonging to VEGF receptor family, receptor belonging to FGF receptor family, growth factor receptor such as NGF receptor family and TGF-$\beta$ super family receptor, receptor of Toll-like receptor family, receptor of LDL receptor association protein family and receptor of G protein conjugate type receptor family, but it is not limited to these.

The present invention provides a technique to read a conformational change in a target protein, which is induced by addition of a compound into a solution of the target protein, from a change in TROSY NMR correlation spectrum (for example, $^1H/^{15}N$-NMR spectrum). By this technique, both of 1) a site on a target protein to which a compound is bound and 2) a structural change in the target protein caused by the compound can be observed at the same time.

Most of proteins develop their function when they are converted into an active structure by a compound such as ligand and agonist. Therefore, a compound which converts the target protein to an active structure can be an agonistic lead compound, and on the other hand, a substance which inhibits the conversion of the target protein to an active structure by ligand, agonist, etc. can be a lead compound for screening a novel antagonist. Therefore, it is important in the screening of new drugs to detect how the structure of the protein changes when a compound is bound or contacted with the target protein.

However, technique of analyzing interaction between a compound and the target protein by existing NMR does not provide quantitative data relating to the change in protein structure. Therefore, a method to detect how the structure of the protein changes when a compound is bound or contacted with the target protein is desired.

The present invention provides a method of determining a structural change of the protein when a compound is bound to the protein by using magnetic nuclear resonance and a method therefor and a program used in the method.

More specifically, the present invention relates to a method of determining a structural change of the protein when an arbitrary compound is contacted with and bound to with the protein by using magnetic nuclear resonance. Furthermore, the present invention provides a method of identifying and screening a compound causing a structural change of the protein when an arbitrary compound is bound or contacted with the protein. In addition, the present invention provides a method of identifying and screening a substance which induces a structural change similar to that induced by a ligand or an agonist, by comparing a structural change when a substance such as, for example, a ligand or an agonist, which is known to induce a structural change in a protein when bound to the protein, is bound to the protein and a structural change when an arbitrary compound is bound to the protein. For example, the present invention provides quantitative information of a change in the protein structure caused by a compound and therefore a screening method which enables identification of an agonistic lead compound.

This method is based on the use of anisotropic spin interaction which is observed by allowing proteins weakly oriented in NMR magnetic field. A number of researches have been reported about acquisition of information on an orientation of each binding axis in the protein from the static magnetic field, which is caused by residual dipole effect, one of the anisotropic spin interaction, and application thereof to the analysis of the protein structure. In addition, technique to decide relative orientation between domains constituting a protein based on the residual dipole effect has been also reported. Observation of the residual dipole effect imposes, however, a theoretical limitation on the molecular weight of the target protein which can be observed and only proteins of about 60 kDa (about 500 residues in the number of amino acid) or less may be observed. Target proteins suitable to screen drugs have a molecular weight much larger than 60 kDa. Therefore, it has been too inadequate in versatility to be applied for screening compounds aimed at drug discovery.

The new technique which is a key in the present invention enables to exceed the application limit of the molecular weight of the target protein which resides in the conventional method and to quantitatively observe relative orientation between domains in a protein caused by a compound even when a protein of 900 kDa or more is directed to theoretically and to determine the a structural change.

For example, the present invention provides a screening technique to search for a lead compound for a novel drug. Specifically, the present invention provides a technique to quantitatively evaluate a structural change of a target protein derived from interaction with a compound by TROSY $^1H/^{15}N$ correlation NMR spectrum or TROSY $^2H/^{15}N$ correlation NMR spectrum. Furthermore, the present invention makes use of this technique and provides a screening method for identifying agonistic lead compound using as an index the presence or absence of the change of the target protein to an active structure.

(NMR Structure Analysis)

As for the protein sample used for higher-order structure analysis by NMR used in this specification, it is usually subjected to structure analysis by labeling with a stable isotope through biosynthesis. Generally, an expression system for the target protein is established at first by genetically manipulating $E.\ coli$, etc., which is then expressed in a culture medium to which carbon sources and nitrogen sources labeled with stable isotopes (glucose in which all carbons are labeled with $^{13}C$ and ammonium chloride in which nitrogens are labeled with $^{15}N$) are added, and thereby proteins with all the carbons and nitrogens labeled with stable isotopes can be obtained. The resulting labeled proteins can be purified by chromatography or the like, concentrated by ultrafiltration and subjected to NMR measurement. On this occasion, it is desirable to pay attention to the following conditions.

As for container to be used, apparatuses to be used including a NMR sample tube is preferably subjected to coating with silicone, etc. to suppress adhesion and spreading of the protein on the glass wall surface in consideration of high viscosity of the protein. It is also desirable to use Pasteur pipettes in handling a sample.

As a solvent, an aqueous solution is usually used. A protein has, however, a lot of exchangeable amide protons and when a heavy water solution is used, amide protons, which are a key factor in the analysis of spectrum, are substituted with deuterium resulting in loss of a lot of information. Therefore, usually a sample is prepared with a light water solution, and then heavy water of on the order of 10% is added for NMR locking. A surfactant, a reducing agent may be added as required.

Sample concentration is usually on the order of 1 mM (for example, 0.4 mM to 2 mM). If the sample is excessively available and solubility is high, measurement can be performed even by 5 mM to 10 mM but it should be noted that association in the solution could occur at a higher concentration. In order to prevent unexpected analysis results resulted by association, it is preferable to compare linearity using samples of a lower concentration and a higher concentration, and to confirm whether association occurs or not.

pH to be used is usually preferably around 5 to 7. For exchanging rate of exchangeable proton such as amide proton is decreased by lowering pH. However, low pH may affect the higher-order structure and therefore, it is preferable to confirm by circular dichroism (CD) spectrum, etc.

As for buffer, those having no protons are preferably used to prevent them from interfering the spectral analysis. Such a buffer includes phosphate buffer, deuteration acetate buffer but it is not limited to these.

The temperature to be used is desirably around 30 to 40° C. to get closer to the temperature in the living body. Because T2 of protein molecule gets longer by setting the temperature rather high and lowering the viscosity of the solution, spectrum is generally obtained in a good condition when the temperature is high.

When dissolved oxygen is contained in the sample solution, relaxation time shortens due to paramagnetic relaxation which causes loss in the sensibility and may be an obstacle to detect the TROSY correlation and therefore, it is preferable to remove dissolved oxygen by deaeration. Deaeration operation includes deaeration under reduced pressure, bubbling of inert gas, and preferably vacuum deaeration is used. It is desirable not to make foams.

For the conservation of solution, it is desirable to add azide, but it is not always necessary to add it.

After a sample is prepared, shimming of NMR is performed. At first NMR locking is made valid and resolution adjustment is performed. Since NMR measurement of a protein solution is observation in a light water solution as a general rule, it is desirable to cancel the huge water signal (with a concentration of $^1H$ higher than the target protein by tens of thousands to millions times). This is performed for the purpose of adjusting resolution, and preferably it is desirable to perform sufficient resolution adjustment for every measured sample in order to obtain high quality spectrum. Usually, the sample tube is not rotated in the measurement of protein solution NMR, it is necessary to surely increase the resolution not only for Z-axis but also for X-and Y-axes as well as adjustment of high ordered term in order to obtain a good spectrum.

Next, pulse width is measured. It is necessary to measure the pulse width for every measured sample in principle since the pulse width may vary for samples according to the difference of salt intensity in the protein solution NMR measured in an aqueous solution.

Since the pulse sequence used in protein solution NMR has a number of RF pulses arranged, it is assumed that shift of pulse width as a total results in considerable influences. Therefore, it is desirable that before carrying out multiple dimension NMR measurement, pulse width is measured with a signal of the target protein and the multiple dimension NMR measurement is performed using the value.

Then the sample is checked by NMR. It is desirable to perform checking by NMR in such a case where the protein may have deteriorated after stored for a certain period of time from the sample preparation.

That is, usually $^{15}N$—$^1H$ HSQC measurement is performed and checking is performed by two-dimensional NMR spectrum. When there are inadequacies found such as inappropriate signal pattern or unmatched phase, adjustment of experimental conditions is again necessary because target protein may be degenerated.

Next, performed is spectral analysis (assignment of signals). Outline of analytical method of spectrum is described below taking NOE spectrum as an example. $^1H$ signals are assigned based on the distance information derived from NOE obtained by NMR and a higher-order structure can be derived. All of the signals overlapped several folds are separated by using 3 dimension measurement, 4 dimension measurement and like and assigned to the known amino acid sequence. The principle is to use the facts that spectrum has a specific pattern for every amino acid and there are extremely characteristic rules in the chemical shifts and spin coupling constants. Automatic assignment is also performed now utilizing such characteristic properties. Characteristic chemical shifts of protein NMR spectrum are shown below.

Chemical shifts of $^1H$ in a protein are generally specified by every environment. In other words, a signal derived from an amide proton (in the neighborhood of 8 ppm), signals derived from an aromatic ring at a side-chain (in the neighborhood of 7 ppm), signals derived from α-position protons (in the neighborhood of 4 ppm), signals derived from β-position protons (in the neighborhood of 2 to 3 ppm) and signals derived from a methyl group (in the neighborhood of 1 ppm) are respectively observed.

There are similar correlations in the chemical shift of $^{13}C$, and in the case of $^{13}C$, it is utilized in various measuring method for assignment by selectively activating each area and handling carbons of α-position and β-position, carbonyl carbon as if they were other nuclides.

As well as assignment of amino acid sequence, a change in the chemical shift derived from higher-order structure is observed. For example, signal derived from a proton at α-position shifts to higher magnetic field in an α-helix structure and shifts to lower magnetic field in β-sheet structure. In addition, there may be a shift around ±1 ppm depending on the positional relationship with an aromatic ring of the side-chain. Further, considerably large shift is observed in metalloprotein at a part where it binds a metal.

Next, spin coupling between the same nuclides should be taken into consideration. Since amino acids constituting protein are linked by a peptide bond (amide bond), spin coupling between $^1H$-$^1H$ is divided by a carbonyl group, and the spin coupling between $^1H$-$^1H$ is limited within the same amino acid residue. Therefore, pattern of spin coupling between $^1H$-$^1H$ is characteristic of each kind of amino acid and amino acids can be identified using this fact. In addition, dihedral angle φ derived from $^3J_{H_\alpha H_N}$ spin coupling constant between α-position proton and amide proton helps to determine the secondary structure of the main chain.

Nuclear spin coupling between different nuclides should also be taken into consideration. Examples of spin coupling constant except $^1H$-$^1H$ related to main chain include H—N (90-100 Hz), N—Cα (11 Hz), Cα-H (140 Hz), Cα-Cβ (30-40 Hz), Cα-C (=O) (55 Hz), Cα-X—N (7 Hz), $^{13}C$—$^{15}N$ (15 Hz)

In addition, NOE correlation should also be taken into consideration. NOE correlation is used for higher-order structure analysis, and $^1H$ same nuclide NOE sandwiching a carbonyl group with amide proton and α-position proton shows that the two protons come from an amino acid residue adjacent to each other through an amide bond, and is used by assignment of amino acid sequence by $^1H$ same nuclide experiment. This technique together with classification information of the amino acid determined based on spin coupling and chemical shift refers to sequence specific chain assignment method.

When assignment procedure is over, higher-order structure analysis is performed if necessary. The higher-order structure of protein includes secondary structure such as α-helix structure and β-sheet structure which amino acid sequence forms with a steric regularity, tertiary structure which some secondary structures are disposed spatially, quaternary structure which domains constructed by tertiary structures are disposed spatially, and it is important to clarify these structures in structure analysis in protein solution NMR measurement, which is performed in various ways according to the purpose.

When the primary sequence is a known amino acid sequence, the way how the known polypeptide chains are entangled with each other to construct a protein is clarified as an image using information provided by NMR. What is used on this occasion is structure optimization calculation algorithm called distance geometry method, molecular dynamics method with binding condition. In either case, these are techniques in which NOE signals as distance information obtained from NMR are gathered as much as possible, which are then given to the calculation program as parameters to work out higher-order structure.

In this specification, the "distance geometry method" refers to a technique which uses a set of distance information and bond angle (dihedral angle) as spatial positional information and the structure is derived based on these. Usually, bond length and bond angle of the covalent bond are fixed at standard values of common proteins, and structural calculation is conducted using the dihedral angle as a variable. Some of the structures which have converged in such a direction as satisfying the binding condition of distance derived from NOE are extracted, and the structure that seems most appropriate is assumed as the final structure. Because this technique involves a little number of variables, calculation is fast, and load on a computer is light, but change of the structure is limited by the contact of atoms (passing between covalent bonds is not possible) and therefore it is difficult to converge into the true structure, and it is used to give the initial structure such as used in molecular dynamics method with binding condition described below.

In this specification, the "molecular dynamics method with binding condition" is one of the molecular dynamics method (method of virtually oscillating molecules to optimize the structure) known as a technique which is generally used to simulate molecular motion and refers to a technique in which the binding condition of distance derived from NOE is added as potential to optimize the structure. Since this technique uses Cartesian coordinates as positional information and involves a number of variables, enormous amount of calculation is needed and load on a computer is heavy, but it is often used at present because calculation time is shortened by rapid progress of computing power of computer.

In this specification, the "simulated annealing method" is one of the techniques of molecular dynamics calculation and refers to a technique in which, unlike common molecular dynamics calculation, parameters contributing to covalent bond are set weak at an initial stage of calculation, temperature of the system is rapidly elevated to aggravate the molecular motion and then the temperature of the system is gradually lowered to slow down the molecular motion as well as to strengthen respective parameter, and thereby converging the structure. According to this, apparent convergence of structure resulted by inhibition of change of structure due to contact of atoms can be prevented.

When the 3-dimension or 4-dimension developed NOE spectrum as mentioned above is observed, detection of correlation correlation signals between different nuclide spins, i.e. $^1H$—$^{15}N$ or $^1H$—$^{18}C$ is basic. When a high molecular weight protein (30 kDa or more) is an object to be analyzed, it becomes difficult to detect these correlation signals between different nuclides due to rapid spin relaxation resulted from shortened T2 relaxation time of each nuclear spin. As a method to solve the problem of rapid spin relaxation which cannot be avoided when a high molecular weight protein is to be observed, and to enable observation of a correlation signal of different nuclides with sufficient observation sensibility even for high molecular weight proteins, TROSY was developed by the group of Wuthrich. This new detection technique of correlation signals between different nuclides can be incorporated into an existing measuring method which has been used for determining conformation of protein till now and the protein structure analysis process mentioned above can be applied to a protein having a molecular weight of 30 kDa or more by changing the data measuring method to a method using TROSY.

Hitherto, NMR techniques usable in this specification are described, but such techniques are well known in the art, and described, for example, Kurt Wuthrich, translated by Yoshimasa Kyougoku/Yuji Kobayashi, NMR of protein and nucleic acid: Structure analysis by two-dimensional NMR, Tokyo Kagaku Dojin, (1991); M. Sattler, J. Schleucher, C. Griesinger, Progr. NMR Spectrosc. 34, 93-158. (1999); J. Cavanagh, W. J. Fairbrother, A. G. Palmer III, N. J. Skelton, Protein NMR Spectroscopy: Principles and Practice, Academic Press. (1995); T. L. James and N. J. Oppenheimer (eds.), Methods in Enzymology, VoL. 239, Academic Press. (1994); Yoji Arata, NMR of protein: Interpretation and estimation of structure data, Kyoritsu Shuppan. (1996); Yoji Arata, Book of NMR, Maruzen. (2000); Nobuaki Nemoto, Takuya Yoshida, Yuji Kobayashi, Kagaku-to-Kogyo (Science and Industry), 69 69 (10), 419-425. (1995); Nobuaki Nemoto, Takuya Yoshida, Yuji Kobayashi, Kagaku-to-Kogyo (Science and Industry), 70 70 (2), 48-55. (1996), which are entirely incorporated in this specification by reference.

(Identification of Lead Compound of Agonist)

One embodiment of identifying a lead compound of agonist is described below. A protein is formed by connecting domains which are partial structures shown as ellipses in FIG. 1. Many proteins, when developing the function, change the relative configuration between these domains into the structure most suitable for developing the function. The induction to the active structure is usually performed by binding of a low molecular weight compound to the protein. An inhibitor binds to the protein but does not induce it to an active structure and functions to maintain the inactive structure. On the other hand, in the case of a compound activating the protein, it binds to the protein and thereby induces a conformational change most suitable for developing the function. Whether the protein structure induced by the binding of a compound is an active structure or not can be judged by using as a template a conformation induced when bound to a natural substrate. The present invention enables to judge whether the protein is in an active structure or not from an easily observable experimental value, i.e. TROSY spectral change by providing NMR analysis technique to quantitatively determine a relative orientation between domains of protein. By using this technique, a lead compound of agonist can be selectively identified based on a relative orientation change between the domains depicted in FIG. 1 as an image.

(Calculation Method of Molecular Orientation of Protein)

Calculation necessary for determining the molecular orientation of protein using an NMR spectrum can be performed, for example as follows, but it is not limited to this.

$\Delta\delta\text{trosy}(k)$, molecular orientation dependent variation of a signal observed on TROSY spectrum in the direction along the $^{15}$N axis can be linked with the two values: residual dipole effect between $^{1}$H—$^{15}$N nuclear spins Dnh and molecular orientation dependent variation of a signal in the direction along the $^{15}$N axis resulted from spatial anisotropy of electron distribution around $^{15}$N nucleus by the following relationship:

$$\Delta\delta\text{trosy}=(\tfrac{1}{2})Dnh+\Delta\delta^{15}N \quad (1)$$

The residual dipole effect $D_{nh}$ can be expressed with an angle $\phi_i$, angle of each NH bond spectrum in the main chain of a protein against the i-th molecule coordinate axis (i=x, y, z) and Saupe order matrix, S defining the orientation of molecules against the external magnetic field ($S_{ij}$ represents an element of molecular orientation matrix; i,j=x, y, z) by the following relationship. $D^0_{nh}$ represents intensity of a dipolar interaction between $^{1}$H—$^{15}$N.

$$D^k_{nh}=D^0_{nh}\Sigma S_{ij}\cos\phi^k_i\cos\phi^k_j \quad (2)$$

i,j=x, y, z

On the other hand, $\Delta\delta^{15}N$, a change in the chemical shift of $^{15}$N derived from the orientation dependent difference of magnetostatic shielding against external magnetic field of $^{15}$N nucleus against external magnetic field, which is resulted from anisotropy of electron distribution around $^{15}$N nucleus, can be expressed with $\sigma_{ij}$ (i,j=x, y, z), elements of chemical shift anisotropy tensor inherent to each peptide bond expressed on molecule coordinate axis and Saupe order matrix defining molecular orientation by the next formula:

$$\Delta\delta^{15}N=(\tfrac{2}{3})\Sigma S_{ij}\delta_{ij} \quad (3)$$

i,j=x, y, z

From the relation of formulae (1) to (3), $\Delta\delta\text{trosy}$, variation of TROSY signal in the direction along the $^{15}$N axis dependent on orientation angle of molecule in the magnetic field, can be expressed by the next formula:

$$\Delta\delta\text{trosy}(k)=\Sigma S_{ij}\{(\tfrac{1}{2})D^0_{nh}\cos\phi^k_i\cos\phi^k_j+(\tfrac{2}{3})\delta_{ij}\} \quad (4)$$

i,j=x, y, z

Using the relationship of formula (4) obtained for plural signals k observed on spectrum and by Singular Value Decomposition, every element $S_{ij}$ of the Saupe order matrix that it is necessary to decide molecular orientation can be determined from experimental value $\Delta\delta\text{trosy}$ and the value $\{(\tfrac{1}{2})D^0_{nh}\cos\phi_i\cos\phi_j+(\tfrac{2}{3})\delta_{ij}\}$ calculated from atomic coordinates within domain structure of the target protein. In this case, the relationship of formula (4) obtained for at least 5, preferably at least 6, more preferably at least 7, at least 8, at least 9, or at least 10 signals of k is used. The relationship of formula (4) can be also used for all signals of k. Information on an orientation of the target protein or domain structures in the target protein against static magnetic field can be obtained by diagonalizing the Saupe order matrix. Physical values obtained here are given as molecular orientation tensor quantity expressed by molecule coordinate axes. This molecular orientation tensor quantity is expressed with molecular orientation intensity (orientation tensor which is a magnitude along each axial direction expressed in three-dimensional-orthogonal coordinate system, and it is quantity to express at what extent the molecule is oriented in the axis (which corresponds to existence probability)) and Euler angles (a, b, c) for the molecule coordinate of new coordinate axis (in which the Z-axis becomes a static magnetic field direction) which describes the oriented state of the molecule. The formula above is illustratively shown with $^{15}$N but it is not necessarily to use $^{15}$N and other stable isotope (for example, $^{13}$C) can be used.

(Determination of Information on an Orientation of Protein)

Figure 2:
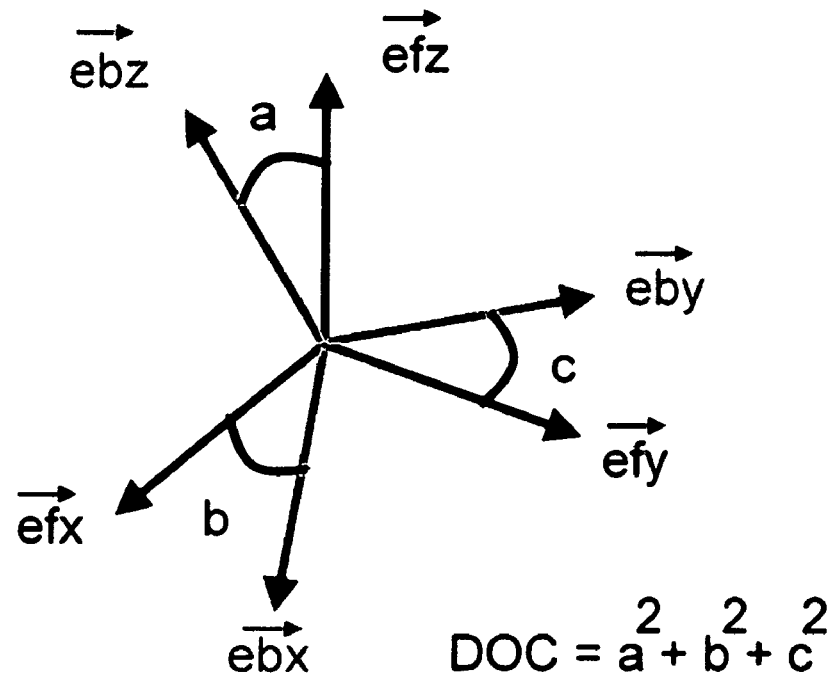
FIG. 2 shows representations of orientation angles for a protein molecule.
Figure 2:
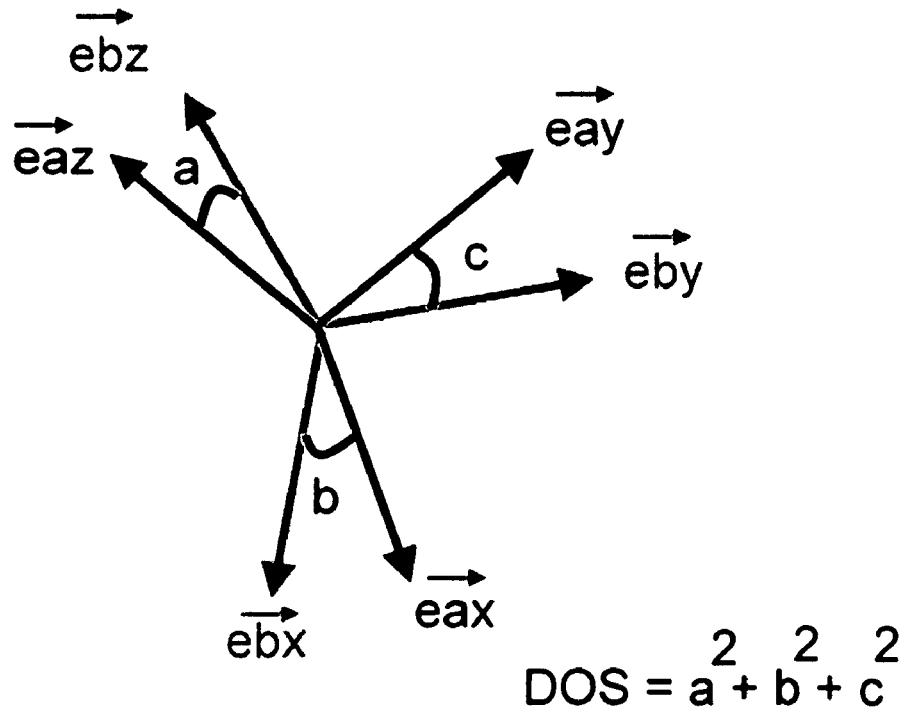

A protein structure is expressed by positions of atoms in x, y, z axes. When the protein is oriented against magnetic field, it is expressed to which extent the coordinate axes (Dxx, Dyy, Dzz) expressing the protein in oriented state tilt from the original. For this purpose, three angles, $\alpha$, $\beta$ and $\gamma$ shown in the drawings are defined. They are called Euler angles. The direction of orientation of the magnetic field is expressed assuming that it agrees with the Dzz axis (FIG. 2).

The index to express a change in the domain structure includes (DOC) and degree of orientational similarity to the active conformation (DOS) in this specification, but it is not limited to these.

In this specification, the "degree of orientational change" (DOC) between two orientations is given by, for example, (i) providing directions of orientation tensor axes by a first three unit vectors perpendicular to each other, by using the first information on an orientation of the domain in the protein before the protein is bound/contacted with the compound, wherein the first three unit vectors are expressed by $$\vec{e}_{fx}, \vec{e}_{fy}, \vec{e}_{fz}$$

(ii) providing directions of orientation tensor axes by a second three unit vectors perpendicular to each other, by using the second information on an orientation of the domain in the protein after the protein is bound/contacted with the compound, wherein the second three unit vectors are expressed by $$\vec{e}_{bx}, \vec{e}_{by}, \vec{e}_{bz}$$

(iii) denoting respective angles between the individual first unit vectors and the individual second unit vectors by a, b and c, and using the angles as an index to express change in the domain structure, or alternatively giving a degree of orientational change by the following equation:

$$\text{degree of orientational change} = a^2 + b^2 + c^2;$$

and using this degree of orientational change as an index to compare the change in the domain structure. For example, when these angles a, b and c are small or when DOC is small, it shows that the structural change of the protein induced by binding/contact of a compound is not significantly different from that in the absence of the compound. Meanwhile, when these angles a, b and c are large or when DOC is large, it shows that the structural change of the protein induced by binding/contact of a compound is significantly different from that in the absence of the compound.

When an agonist compound is screened, similarity of the structural change induced by binding of a ligand and the active structure can be used as an index. In this case, providing a third unit vectors which express each axis of molecular orientation tensor defining domain orientation of active structure after binding/contacting with a ligand by $$\vec{e}_{ax}, \vec{e}_{ay}, \vec{e}_{az}$$

as well as using a second unit vectors after binding/contacting with a compound and denoting respective angles between the respective two unit vectors by a, b and c, and using the angles as an index to express change in the domain structure, or alternatively giving a degree of orientational similarity to the active conformation (DOS) by the following equation:

$$\text{degree of orientational similarity to the active conformation} = a^2 + b^2 + c^2;$$

and using this degree of orientational change as an index to compare the change in the domain structure. For example, when these angles a, b and c are small or when DOS is small, it shows that the structural change of the protein induced by binding/contact of a compound is close to the structural change of the protein induced by the ligand. That is, it can be an index showing similarity of the structural change.

In addition, the structural change of a domain in the protein is digitalized as difference of DOC and/or DOS based on the information on an orientation in each state of the domain to be compared.

Accordingly, when the change of the structure of the protein in the case that the first compound and the protein are contacted and the change of the structure of the protein in the case that the second compound and the protein are contacted are compared, "similarity" in the structural change of the protein means that the difference of DOS as the index of the structural change is small in this specification. For example, a second compound capable of inducing a structural change in a protein when it is contacted with the protein, similar to that induced in the protein when the first compound and the protein are contacted, can be selected as follows:

(a) selecting a domain in the protein;
(b) providing information on an orientation of the domain when the protein is in contact with the first compound;
(c) providing information on an orientation of the domain when the protein is in contact with the second compound, by
  (i) providing known atomic coordinates for the domain,
  (ii) providing axial variations of NMR signals, which are generated from the protein in contact with the second compound in the presence of a liquid crystalline material by two-dimensional TROSY NMR spectroscopy and depend on an orientation angle of the molecules in a magnetic field,
  (iii) determining Saupe order matrix elements for the domain from the atomic coordinates for the domain and the axial variations of NMR signals, and
  (iv) diagonalizing the determined matrix to produce the information on an orientation of the domain; and
(d) comparing DOS between the atomic coordinates provided in step (b) and the atomic coordinates provided in step (c).

Therefore, in the case where the structural change caused by the first compound and the structural change caused by the second compound are identical, a=b=c=0 and therefore, DOS=0. The case where the structural change caused by the first compound and the structural change caused by the second compound is "similar" includes cases where, for example, value of DOS is 75 (deg$^2$) or less, 48 (deg$^2$) or less, 27 (deg$^2$) or less, 12 (deg$^2$) or less, 3 (deg$^2$) or less, 0.75 (deg$^2$) or less, 0.48 (deg$^2$) or less, 0.27 (deg$^2$) or less, 0.12 (deg$^2$) or less or 0.03 (deg$^2$) or less.

Alternatively, whether the structural changes are similar or not can be judged by, for example, calculating DOS between the second compound and the first compound in the group of plural candidate compounds and assuming that the second compound which results in a relatively small DOS or the smallest DOS causes structural change which is similar to the structural change of the target protein caused by the first compound.

(Acquisition of Atomic Coordinates of Protein)

Group of M, Grestein of Yale University, USA collected the interdomain structure and function of a protein as a database named molMovDB.

For example, information on GroEL, adenylate kinase, calmodulin, HIV-1 reverse transcriptase, citrate synthase, diphtheria toxin, HIV-1 protease, EGF-receptor, hexokinase, glucokinase, EPO receptor, phosphoglycerate kinase, recoverin, mRNA capping enzyme, DNA polymerase β are available from a database.

(Method of Obtaining Information on an Orientation of Protein Domain from Atomic Coordinates of Protein)

When atomic coordinates of a protein are obtained by the method mentioned above, information on an orientation of domains of the protein can be obtained from the atomic coordinates. For example, the residual dipole effect $D_{nh}$ can be expressed with an angle $\phi_i$, angle of each NH bond spectrum in the main chain of a protein against the i-th (i=y, y, z) molecule coordinate axis and Saupe order matrix, S defining orientation of molecule against the external magnetic field ($S_{ij}$ represents an element of molecular orientation matrix; i,j=x, y, z) by the following relationship.

$$D^k_{nh} = D^0_{nh} \Sigma S_{ij} \cos \phi^k_i \cos \phi^k_j \quad (5)$$

i,j=x, y, z

Accordingly, every element $S_{ij}$ of the Saupe order matrix that is necessary to define molecular orientation can be determined from $\cos \phi^k_i \cos \phi^k_j$ calculated from atomic coordinates of domain of the protein, residual dipole effect $D_{nh}$ between $^1H$—$^{15}N$ nuclear spins and intensity of residual dipole effect $D^0_{nh}$ between $^1H$—$^{15}N$.

(Method of Identifying a Binding Position on a Protein when a Compound has been Bound to the Protein)

When a compound has been bound to a protein, the binding position on the protein can be determined, for example, according to a process as follows:
  providing a two-dimensional TROSY NMR spectrum of the protein in the absence of a compound,
  providing a two-dimensional TROSY NMR spectrum of the protein in contact with a compound,
  comparing the two-dimensional TROSY NMR spectra each provided above, and detecting a change of the spectra,
  identifying an amino acid residue (preferably, more than one amino acid residue) around the site on the protein to which the compound is bound, by determining in which amino acid residue an atom that has produced a spectral change is contained by assignment of the two dimensional NMR,
  if necessary, comparing the conformation of the compound with the conformation of the protein around amino acid residue specified above and estimating the conformation when the compound binds to the binding site on the protein.

(Observation of a Structural Change in a Domain of a Protein)

According to one aspect of the present invention, structural change in a domain of the protein can be measured and/or a compound which results in structural change (preferably, desired structural change) can be selected, for example, by taking the following steps:
  (a) selecting a domain in the protein;
  (b) providing information on an orientation of the domain when the protein is not in contact with the compound;
  (c) providing information on an orientation of the domain when the protein is in contact with the compound, by
    (i) providing known atomic coordinates for the domain,
    (ii) providing axial variations of NMR signals, which are generated from the protein in contact with the compound in the presence of a liquid crystalline material by two-dimensional TROSY NMR spectroscopy and depend on an orientation angle of the molecules in a magnetic field,
    (iii) determining Saupe order matrix elements for the domain from the atomic coordinates for the domain and the axial variations of NMR signals, and
    (iv) diagonalizing the determined matrix to produce the information on an orientation of the domain; and
  (d) measuring the structural change in the protein by a difference between the atomic coordinates provided in step (b) and the atomic coordinates provided in step (c).

As for domains to be observed by the process of the present invention, any domain in the protein to be observed is usable. However, for example, the domain to be observed is preferably, for example, a domain producing a large change in the information on an orientation depending on the presence or absence of the compound and/or a domain producing a different change in the information on an orientation by binding to a different compound.

The above step (b) in the above measuring process may be, if necessary,
  (b) providing the information on an orientation of the domain when the protein is not in contact with the compound, by
    (v) providing known atomic coordinates for the domain,
    (vi) providing axial variations of NMR signals, which are generated from the protein in no contact with the compound in the presence of the liquid crystalline material by two-dimensional TROSY NMR spectroscopy and depend on the orientation angle of the molecules in the magnetic field,
    (vii) determining Saupe order matrix elements for the domain from the atomic coordinates for the domain and the axial variations of NMR signals, and
    (viii) diagonalizing the determined matrix to produce the information on an orientation of the domain; or
  (b) providing the information on an orientation of the domain from the atomic coordinates provided previously when the protein is not in contact with the compound. The TROSY spectrum to determine plural Saupe order matrix elements as above can be measured at the same time or separately.

In addition, variations of NMR signal in the axial direction, which are generated in the above step (b) and/or (c) by two dimensional TROSY NMR spectroscopy and depend on the orientation angle of the molecules in the magnetic field, may be variations in the $^{15}N$ axial direction if $^{15}N$ is used. When the nuclide of another stable isotope is used, it may be variations in the axial direction of the nuclide.

Here, when $^{15}N$ is used, the Saupe order matrix elements in (iii) and/or (vii) are preferably determined by:
  with respect to the kth pair of $^{15}N$ nuclear spins in the domain,
  providing $\phi^k_i$ as a vector angle of an N—H bond having the kth pair of spins in the domain to the ith molecular axis,
  providing $\phi^k_j$ as a vector angle of an N—H bond having the kth pair of spins in the domain to the jth molecular axis,
  setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å,
  determining as $\delta_{ij}$ a tensor value for chemical shift anisotropy of a $^{15}N$ nucleus in an arbitrary residue of the protein, and
  determining the Saupe order matrix elements $S_{ij}$ defining the molecular orientation with respect to the magnetic field, by contacting the protein with the compound in the presence of the liquid crystalline material, providing $\Delta\delta$trosy(k) for the kth pair of $^{15}N$ nuclear spins of the protein by two-dimensional TROSY NMR spectroscopy, and using the $\Delta\delta$trosy(k) together with the following equation (1):

$$\Delta\delta\text{trosy}(k) = \Sigma S_{ij}\{0.5 D^0_{nh} \cos \phi^k_i \cos \phi^k_j + (2/3)\delta_{ij}\} \quad (1)$$

i, j=x, y, z

When a nuclide of stable isotope other than $^{15}N$ is used, the above calculation may be performed for the spin pair of the nuclide. In that case, since the distance of the other different nuclides bond corresponding to the distance of N—H bond and static bipolar coupling are known, the known value can be used in the above equation.

The structural change in a domain of a protein is provided by, for example, diagonalizing the Saupe order matrix elements to produce information on an orientation of the domain. Therefore, different pieces of information on an orientation of the domain in itself can be compared to produce an index of a structural change in the domain. For example, when there is a change in information on an orientation of the predetermined domain between in the presence of and in the absence of a compound, it turns out that the compound has brought about the structural change of the predetermined domain when it was bound to a protein. The information on an orientation in the presence of and in the absence of a compound can be experimentally obtained respectively, but, for example, when information on an orientation under in the absence of the compound is already provided by NMR experiment or X-ray analysis, the information can be used and compared with information on an orientation provided by experiment in the presence of the compound.

Furthermore, DOC and DOS can be used as an index of the structural change. Therefore, DOC can be used as the size of the structural change that an arbitrary compound induces. When the value of DOC is large, it shows that the structural change is large. In addition, DOS can be used to find whether an arbitrary compound produces a change of the structure similar to that of a certain ligand or agonist. When the value of DOS is smaller, it shows that the structural change resembles more.

Screening of an agonistic agent which induces the target protein into activation can be performed, for example, by the following procedure:

providing information on an orientation (A) of domain in the target protein under the condition in which a ligand or agonist known to induce structural change of domain binds to the target protein;

providing information on an orientation (B) of domain in the target protein under the condition in which the candidate compound of screening binds to the target protein;

comparing the information on an orientation (A) and (B) and determining whether the information on an orientation is equivalence or similar.

when these pieces of information on an orientation are equivalence or similar, it turns out that the candidate compound is a compound inducing a structural change of target protein which is similar to that of an agonist inducing the target protein to be active. Therefore, the candidate compound selected in this way is a useful agonistic lead compound.

In the present invention, a step for specifying the position at which the compound binds to the protein can be performed if necessary. The specification of the position is performed, for example, by comparing the two dimension TROSY NMR spectrum provided in step (b) and the two dimension TROSY NMR spectrum provided in step (c) to detect a change in the spectrum and identify the amino acid residue in the protein which has produced the change in the spectrum. Identification of this amino acid residue is performed based on the assignment of the changed spectrum to the amino acid sequence.

The liquid crystal material used in the present invention includes a mixture selected from the group consisting the following:

a mixture of dimyristoylphosphatidylcholine (DMPC) and dihexanoylphosphatidylcholine (DHPC), a mixture of dimyristoylphosphatidylcholine (DMPC) and dihexanoylphosphatidylcholine (DHPC) and sodium dodecyl sulfate (SDS), a mixture of dimyristoylphosphatidylcholine (DMPC) and dihexanoylphosphatidylcholine (DHPC) and cethyltrimethyl ammonium bromide (CTAB), a mixture of 1,2-di-O-dodecyl-sn-glycero-3-phosphocholine (DIODPC) and 3-(cholamidepropyl)-dimethylammonio-2-hydroxy-1-propane sulfate (CHAPS), a mixture of n-alkyl-poly(ethyleneglycol)/n-alkyl alcohol, filamentous phage, a mixture of cetyl pyridinium chloride (CPCl)-hexanol-NaCl a mixture of cetyl pyridinium bromide (CPBr)-hexanol-NaCl, purple membrane fragments of *Halobacterium* genus, microcrystalline cellulose and polyacrylamide gel (for example, acrylamide/acrylate gel) and a mixture of at least 2 of the above mixtures.)

For example, the liquid crystal material is a mixture of 7.5% (w/v) of dimyristoylphosphatidylcholine (DMPC) and dihexanoylphosphatidylcholine (DHPC) and cethyltrimethyl ammonium bromide (CTAB).

In another aspect of the present invention, a program carrying out the process of the present invention and a storage medium including such a program are also provided.

In a still further aspect of the present invention, a device which can be used to carry out the process of the present invention and a device including the program of the present invention are provided.

The present invention is described in detail below by way of Examples and the like, but the present invention is not limited to these.

EXAMPLE 1

(Orientation of Protein by Liquid Crystal Material)
Orientation of a protein by a liquid crystal material is performed by the following method, for example.
(1. Weak Orientation of a Protein Using a Mixture of Dimyristoylphosphatidylcholine (DMPC) and Dihexanoylphosphatidylcholine (DHPC))

DMPC and DHPC are mixed preferably at a pH of 6.8 to 8.0, more preferably at pH 6.5, preferably at a mixing ratio of 2.5 to 3.0, more preferably at a mixing ratio 3.0. This mixture is used preferably at a concentration of 5 to 20% (w/v), more preferably at a concentration of 7.5% (w/v), and molecular orientation is performed preferably at 25 to 40° C., more preferably at 30° C. (M. Ottinger and A. Bax, J. Biomol. Nuclear magnetic resonance 12, 361 (1998)).
(2. Weak Orientation of a Protein Using a Mixture of Dimyristoylphosphatidylcholine (DMPC) and Dihexanoylphosphatidylcholine (DHPC) and Sodium Dodecyl Sulfate (SDS))

For example, a surfactant such as SDS is added to a DMPC/DHPC solution of above 1 and the surface of phospholipid membrane is negatively charged to prevent unnecessary adsorption to phosphatide of a protein having negative surface charge. When SDS is added, mixing with a protein sample solution is performed also preferably at a pH of 6.0 to 8.0, more preferably at pH 6.5, preferably at a concentration of 5 to 20% (w/v), more preferably at a concentration of 7.5% (w/v), and molecular orientation is performed preferably at 20 to 35° C., more preferably at 30° C. In this case, DMPC and DHPC are mixed preferably at a mixing ratio of 2.5 to 3.0, more preferably at a mixing ratio 3.0. Preferably SDS is added to DMPC at a ratio of 1 to 3%. (J. A. Losonczi and J. H. Prestigard, J. Biomol. Nuclear magnetic resonance 12, 447 (1998))

(3. Weak Orientation of a Protein Using a Mixture of Dimyristoylphosphatidylcholine (DMPC) and Dihexanoylphosphatidylcholine (DHPC) and Cethyltrimethyl Ammonium Bromide (CTAB))

For example, a surfactant such as CTAB is added to a DMPC/DHPC solution of above 1 to prevent unnecessary adsorption to phosphatide of a protein having positive surface charge. When CTAB is added, mixing with a protein sample solution is performed also preferably at a pH of 6.0 to 8.0, more preferably at pH 6.5, preferably at a concentration of 5 to 20% (w/v), more preferably at a concentration of 7.5% (w/v), and molecular orientation is performed preferably at 20 to 35° C., more preferably at 30° C. In this case, DMPC and DHPC are mixed preferably at a mixing ratio of 2.5 to 3.0, more preferably at a mixing ratio 3.0. Preferably CTAB is added to DMPC at a ratio of 1 to 3%.
(J. A. Losonczi and J. H. Prestigard, J. Biomol. Nuclear magnetic resonance 12, 447 (1998))

(4. Weak Orientation of a Protein Using a Mixture of 1,2-di-O-dodecyl-sn-glycero-3-phosphocholine (DIODPC) and 3-(cholamidepropyl)-dimethylammonio-2-hydroxy-1-propane Sulfate (CHAPS))

The ratio of DIODPC/CHAPSO is most appropriately 4.8, but it is not limited to this. The concentration of phospholipid membrane in the sample is most appropriately 5% (w/v), but it is not limited to this. Preferably pH of the sample solution is 1.0 to 6.5. Molecular orientation is preferably in the range of 10 to 60° C. (S. Cavagnero et al., J. Biomol. NMR 13, 387 (1999))

(5. Weak Orientation of a Protein Using a Mixture of n-alkyl-poly(ethyleneglycol)/n-alkylalcohol)

The alcohol mixture mentioned above is not limited, but molecular orientation can be induced preferably by adding 5% (w/v) to the solution in the range of 0 to 40° C. As for the kind of alcohol, n-hexanol or n-octanol can be used. The ratio of n-alkyl-poly(ethyleneglycol)/n-alkylalcohol is preferably in the range of 0.6-0.9. As for pH, any pH can be used. (M. Ruckert and G. Otting, J. Am. Chem. Soc. 122, 7793 (2000))

(6. Weak Orientation of a Protein Using Filamentous Phage)

Molecular orientation in the magnetic field can be realized by letting a bacteriophage having a fibrous shape such as pf1 or tobacco mosaic virus (TMV) coexist in the sample solution. Preferably bacteriophage concentration in the sample solution is in the range of 10 to 50 mg/ml. Preferably the concentration is 25 mg/ml. Preferably pH is equal to or less than 6. Any temperature can be used, but preferably it is used in the range of 20 to 40° C. (Hansen et al., Nat. Struct. Biol. 5, 1,065 (1998); Clore et al., J. Am. Chem. Soc. 120, 10,571 (1998))

(7. Weak Orientation of a Protein Using a Cetyl Pyridinium Chloride (CPCl)-hexanol-NaCl Mixture or Cetyl Pyridinium Bromide (CPBr)-hexanol-NaCl Mixture)

CPBr: hexanol=1:1.33 (w/w) to 1:1 (w/w) is used. The concentration of NaBr is preferably 25 to 40 mM, and the concentration of NaCl is preferably 200-500 mM. The concentration when this liquid crystal material is used is preferably 1 to 10% (w/v), and molecular orientation is preferably performed at a temperature in the range of 15 to 50° C.

(8. Weak Orientation of a Protein Using a Purple Membrane Piece of Genus *Halobacterium*)

A purple membrane piece of genus *Halobacterium*, preferably a purple membrane piece of *Halobacterium salinarium* is used at a concentration of 1 to 10 mg/ml. Any solution temperature and any pH can be used. Preferably NaCl concentration in the solution is 50 mM or less. (Prosser et al., J. Am. Chem. Soc. 120, 11010 (1988))

(9. Weak Orientation of a Protein Using Microcrystalline Cellulose)

Preferably a solution of 80 mg/ml is prepared and molecular orientation is possible by introducing a protein. Any pH and temperature can be used. When the ion concentration of the solution increases, the sample solution which is necessary to realize molecular orientation is added. (Fleming et al., J. Am. Chem. Soc. 122, 5224 (2000))

(10. Weak Orientation of a Protein Using Polyacrylamide Gel)

A protein solution is injected into polyacrylamide gel which has been compressed in longitudinal or lateral direction in a NMR sample tube and a protein is automatically subjected to molecular orientation. Any pH, ionic strength and observation temperature can be used. (Saas et al., J. Biomol. NMR 18, 303 (2000); Tycko et al., J. Am. Chem. Soc. 122, 9340 (2000))

(11. Orientation of a Protein Using Acrylamide/Acrylate Gel)

As an example of polyacrylamide gel, a gel as alignment medium may be used which is prepared by stretching 50% acrylamide/50% acrylate gel by 2.5 times. When the acrylamide/acrylate is gelled, a labeled protein may be added to orient the protein in the gel.

EXAMPLE 2

(Comparison of Information on a Molecular Orientation Obtained from TROSY Signal Change with the Results of Conventional Analysis)

0.5 mM ubiquitin (8.6 kDa) was dissolved in a 20 mM sodium phosphate buffer solution (pH 6.4) and 7.5% (w/v) of DMPC/DHPC/CTAB was added to form a molecular orientation state at 30° C. and the solution was tested by the following procedure.
(Experiment)
(NMR Spectroscopy)

All the spectra used by this analysis were recorded at 30° C. under the condition in which a bicelle mixture of dimyristoylphosphatidylcholine (DMPC) and dihexanoylphosphatidylcholine (DHPC) doped with cethyltrimethyl ammonium bromide (CTAB) was arranged so that it gave 10 Hz of residual quadrupole splitting in $^2$HNMR spectrum. Data acquisition was carried out on the Varian INOVA500 spectroscope with $^1$H frequency operated at 499.84 MHz. The present inventors used $^1$H detection coil Varian gHX Nano-Probe equipped with X adjusted to $^{15}$N for magic angle test. Sample rotating speed was set to 2.6 kHz and the torque caused by having arranged bicelle with regard to the magnetic field was removed (Courtieu, J., Bayles, J. P.; Fung, B. M., Prog. NMR spectrosc. 1994, 26, 141-169; Kurita, J., Shimahara, H. Utsunomiya-Tate, N.; Tate, S. J. MagnReson. 2003, 163, 163-173). $^1$H—$^{15}$N dipole coupling was measured in $^1$H—$^{15}$N IRAP-HSQC spectrum (Ottiger, M.; Delaglio, F.; Bax, A. J. Magn Reson. 1998, 131, 373-378). $^1$H—$^{15}$N TROSY spectrum (Pervushin, K.: Riek, R.; Wider, G.; Wuthrich, K. Proc. Natl. Acad. Sci. U.S.A 1997, 94, 12366-12371, Weigelt, J. J. Am. Chem. Soc. 1998, 120, 10778-10779) was collected in both isotropic state and anisotropic state using a solution of 50 mM sodium phosphate (pH 6.4) containing 7.5% (mass/volume) of DMPC:DHPC:CTAB bicelle and the same solution containing 0.5 mM $^{15}$N labeled ubiquitin dissolved in 2 mM EDTA as sample solutions without using magic angle sample rotation method.

All the data was processed using NMRpipe program software package (Delaglio, F.; Grzesiek, S.; Vuister G. W.; Zhu, G.; Pfeifer, J.; Bax, A. J. Biomol. NMR 1995, 6, 277-293). Peak position was determined by fitting an ellipse to each of the calculated contour between 60% and 80% of the peak maximum using program PIPP (Garrett, D. S.; Powers, R.; Gronenborn, A. M.; Clore, G. M, J. Magn. Reson. 1991, 95, 214-220). The center of each ellipse provides criterion of peak position and values obtained for all contours in the intensity range of 60 to 80% of the predetermined peak were averaged so as to provide peak position. Acquisition time data for acquisition at $t_1$ dimension and at $t_2$ dimension was 111 ms and 128 ms respectively and had a matrix size of 200 ($t_1$, $^{15}N$)×1024 ($t_2$, $^1H$) complex points. The final processed data widely zero-filled showed digital resolution of 2.0 Hz and 0.88 Hz for $^1H$ dimension and $^{15}N$ dimension respectively.

(Calculation of Sequence Tensor)

Determination of sequence inductive TROSY shift change and lining-up tensor derived from error estimation was carried out by in-house C-program incorporated into a public subroutine (Press, W. H.; Teukolsky, S. A.; Vetterling, W. T.; Flannery, B. P. Numerical recipes in C 2nd ed.; Cambridge university press: New York, 1992). Sequence tensor was calculate from experimental data, and calculated from reference structure generated by 1.8 Å X-ray coordinate (PDB entry code, 1UBQ) (Vijay-Kumar, S. Bugg, C. E.; Cook, W. J. J. Mol. Biol. 1987, 194, 531-544) having a hydrogen atom added by program MOLMOL (Koradi, R.; Billeter, M.; Wuthrich, K. J. Mol. Graph. 1996, 14, 51-55.) The effect of TROSY shift on experimental indeterminacy was evaluated by repeating specific value decomposition (SVD) calculation (Losonczi, J. A.; Andrec, M.; Fischer, M. W.; Prestegard, J. H. J. Magn. Reson. 1999, 138, 334-342) on the generated data set. This data set was generated by adding Gaussian noise to the experimental data. Gaussian noise was assumed to distribute in a relative probability ($-\exp(x^2/2\delta^2)$). Here, x is an experimental value, and $\delta$ is a rms noise estimated from rms deviation of TROSY shift during continuous experiments.

"Structural noise" was simulated by reorienting NH binding vector in a random manner by a method similar to that described in reference (Zweckstetter, M.; Bax, A. J. Biomol. Nuclear magnetic resonance, 2002, 23, 127-137). The deviation between the original vector and the reoriented vector was described with a circular cone having 5 degrees slope angle from the original direction. Slope angle between the original NH vector and the reoriented NH vector is assumed to be in Gaussian distribution ($-\exp(\alpha^2/2\theta^2)$) in the simulation of this structure noise. Here, $\alpha$ is a slope angle and $\theta$ is an estimated standard deviation for a slope angle fixed to five degrees. The angle of rotation in the lateral direction of vector reoriented in the circular cone was simulated assuming that it was uniformly distributed. Selection of appropriate values from the simulated data was performed by maintaining the rms deviation between the experimental data and simulated $\Delta\delta_{trosy}$ value to less than 2.55 Hz. This value shows a rate accepted for 68% of the simulated values, and this value means that these values are present within one standard deviation of average.

$\Delta\delta_{trosy}$ values for $^{15}N$ labeled ubiquitin dissolved in 7.5% (w/v) DMPC/DHPC/CTAB bicelle at 30° C. are shown in the following Table.

TABLE 1

| Residue | $\Delta\delta_{trosy}$/Hz |
|---|---|
| 13 ILE | 0.64 |
| 14 THR | 3.01 |
| 15 LEU | 1.54 |

TABLE 1-continued

| Residue | $\Delta\delta_{trosy}$/Hz |
|---|---|
| 16 GLU | 1.86 |
| 17 VAL | -0.76 |
| 18 GLU | -3.08 |
| 20 SER | -2.47 |
| 21 ASP | 4.81 |
| 23 ILE | 0.04 |
| 25 ASN | -1.66 |
| 26 VAL | 0.97 |
| 27 LYS | 0.66 |
| 28 ALA | 0.82 |
| 29 LYS | 0.04 |
| 30 ILE | 2.33 |
| 31 GLN | 2.40 |
| 32 ASP | -1.96 |
| 33 LYS | 0.77 |
| 34 GLU | 1.32 |
| 35 GLY | -0.54 |
| 36 ILE | -3.50 |
| 39 ASP | 3.12 |
| 40 GLN | -2.63 |
| 42 ARG | 4.90 |
| 44 ILE | 2.05 |
| 45 PHE | -0.23 |
| 47 GLY | 2.59 |
| 48 LYS | -5.99 |
| 49 GLN | -2.63 |
| 50 LEU | 0.31 |
| 51 GLU | -2.01 |
| 54 ARG | 2.75 |
| 55 THR | 0.23 |
| 56 LEU | 1.72 |
| 57 SLR | 5.55 |
| 58 ASP | 1.02 |
| 59 TYR | 2.36 |
| 60 ASN | 4.69 |
| 61 ILE | 5.74 |
| 62 GLN | 6.21 |
| 63 LYS | -5.80 |
| 64 GLU | 2.27 |
| 65 SER | 6.61 |
| 66 THR | 4.90 |
| 67 LEU | 4.34 |
| 68 HIS | 0.54 |
| 69 LEU | 1.09 |
| 70 VAL | 2.00 |
| 71 LEU | 2.01 |
| 72 ARG | 4.93 |

In the experiment which gave the above results, experiment was performed without applying MAS or by applying MAS respectively for obtaining data collected in an anisotropic state and aligned state. MAS (magic angle sample spinning) is an abbreviation of magic angle sample spinning. When NMR measurement is performed with MAS applied, molecular orientation can be physically cancelled even if a liquid crystal material coexists. Therefore the same data in the case where a liquid crystal material does not coexist can be obtained even if a liquid crystal material coexists.

$\Delta\delta_{trosy}$ value was calculated from a series of $^1H$—$^{15}N$ TROSY data by $\Delta\delta_{trosy}$ value=$\delta^{15}N_{trosy}$ (MAS not applied)−$\delta^{15}N_{trosy}$ (MAS applied)

Determination of Saupe order matrix element was performed as follows.

With respect to the kth pair of $^{15}N$ nuclear spins in the domain, providing $\phi^k_i$ as a vector angle of an N—H bond having the kth pair of spins in the domain to the ith molecular axis, providing $\phi^k_j$ as a vector angle of an N—H bond having the kth pair of spins in the domain to the jth molecular axis, setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å determining as $\delta_{ij}$ a tensor value for chemical shift anisotropy of a $^{15}N$ nucleus in an arbitrary residue of the protein, and determining the Saupe order matrix elements $S_{ij}$ defining the molecular orientation with respect to the magnetic field, without contacting the protein with the compound in the presence of the liquid crystalline material, providing $\Delta\delta$trosy (k) for the kth pair of $^{15}N$ nuclear spins of the protein by two-dimensional TROSY NMR spectroscopy, and using the $\Delta\delta$trosy(k) together with the following equation (1):

$$\Delta\delta\text{trosy}(k) = \Sigma S_{ij}\{0.5 D^0_{nh} \cos\phi^k_i \cos\phi^k_j + (2/3)\delta_{ij}\} \quad (6)$$

i, j=x, y, z

Euler angles α, β, γ were obtained by diagonalizing this S.

The molecular orientation angle of ubiquitin determined from TROSY signal change induced by this molecular orientation was obtained from conventional residual dipole effect observation.

The residual dipole effect observation was performed by observing the intensity change shown by $^1$Jnh (single bond spin coupling constant between $^1H$—$^{15}N$ nuclear spins) of signals derived from each amino group which are observed before and after inducing molecular orientation by using liquid crystal molecules following a conventional residual dipole effect observation method: IPAP-HSQC method (In-phase-Antiphase mode Heteronuclear Single Quantum Coherence spectroscopy; Ottiger et al., J. Magn. Reson. 131, 373 (1998)) and calculating the residual dipole effect $D_{nh}$ between each of the $^1H$—$^{15}N$ nuclear spins using $^1$Jnh (aniso) observed in the molecular orientation state with liquid crystal and $^1$Jnh (iso) observed when it is not in the molecular orientation state without liquid crystal, in the following equation:

$$D_{nh} = {}^1Jnh(\text{aniso}) - {}^1Jnh(\text{iso})$$

The results of having compared it with molecular orientation angle provided from residual dipole effect observation are as follows. (tilt of molecular orientation axis with regard to the molecule coordinate axis is shown in Euler angles expression).

TABLE 2

| Process | Euler angle | | |
|---|---|---|---|
| | α/deg. | β/deg. | γ/deg. |
| The inventive technique | 70.6 ± 3.8 | 69.7 ± 2.1 | 78.7 ± 2.3 |
| Prior Art | 73.1 ± 1.3 | 70.3 ± 1.0 | 78.9 ± 1.1 |

From these results, it was confirmed that molecular orientation angle information determined based on a TROSY signal change gave results which are consistent to conventional molecular orientation determination technique. In other words, it has been shown for high molecular weight protein that the structural change of the target protein induced by binding to a compound can be quantitatively observed only by a TROSY signal change.

EXAMPLE 3

(Observation of Structural Change for High Molecular Weight Protein Using the Present Invention)

Information on an orientation of protein having molecular weight more than 30 kDa which was not able to measure by conventional NMR was obtained by the present invention and a structural change was measured as follows.

As an object protein, mRNA5'-capping enzyme (PBCV1-CE) which is a guanylyl transferase of chlorella virus PBCV1 having molecular weight of 35 kDa was used. Molecular weight of 35 kDa is a molecular weight region in which it becomes difficult to analyze molecular orientation by conventional measuring methods. It is well known that activity is controlled in this protein depending on a change of conformation induced by a ligand. It has been made clear that PBCV1-CE which is not bound to a ligand takes two structures (an open type and a closed type) in the crystal by crystallography. In this example, structure in a solution of PBCV1-CE in the coexistence of pyrophosphoric acid which is binding inhibitor of GTP which induces an active form structure was analyzed and a change from the structure which did not have a ligand was analyzed.

(Assignment of Main Chain)

Because assignment data of main chain was necessary for data analysis of TROSY measurements, about 50% of the main chain was assigned using PBCV1-CE triplexly labeled with $^2H/^{13}C/^{15}N$.

(Conditions for TROSY Measurements)

Figure 3:
FIG. 3 is a photograph of a gel as alignment medium used in Example 3, where a white bar on the upper right shows a length of 10 mm.
Figure 4:
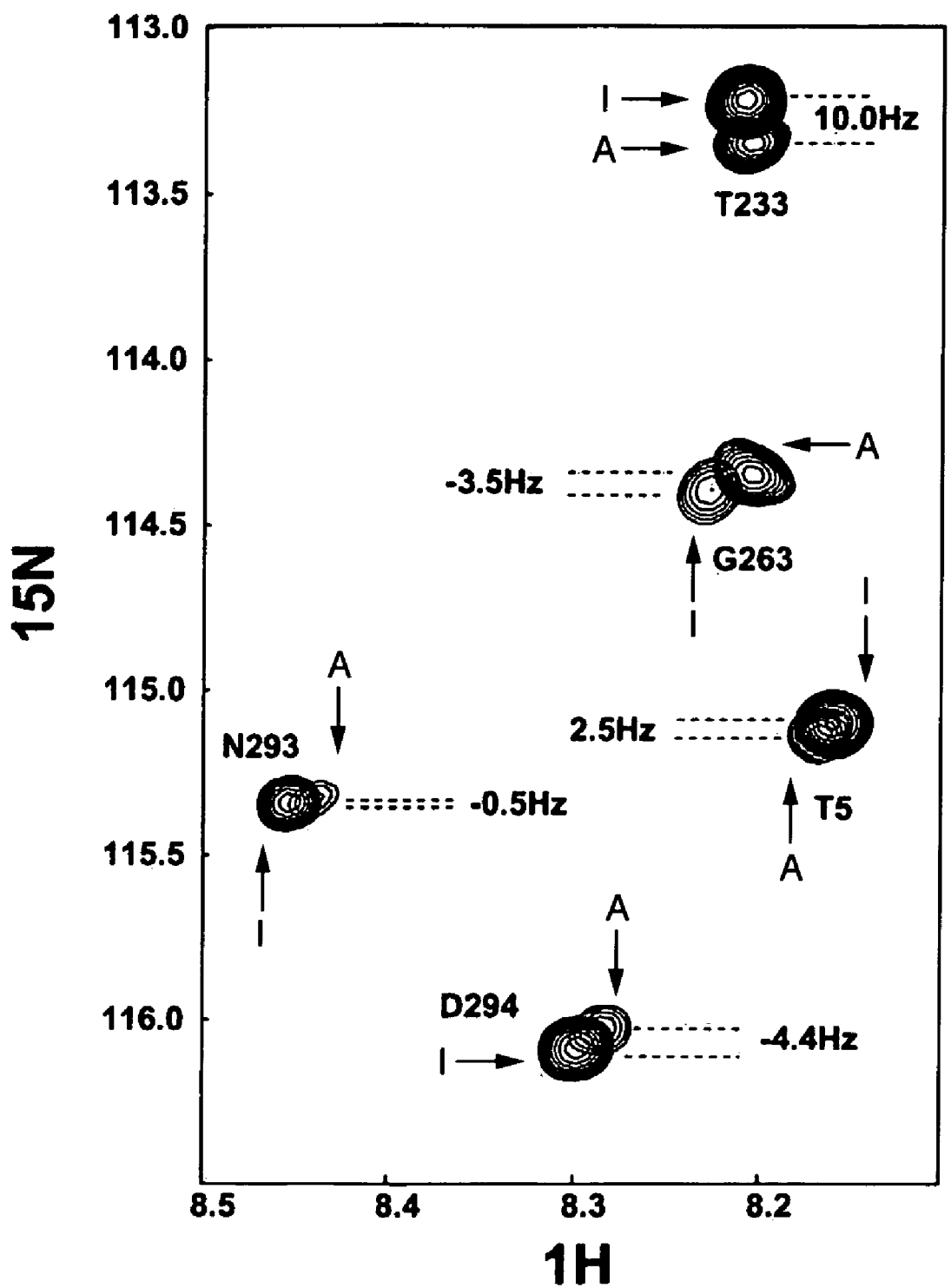
FIG. 4 shows TROSY signals of an mRNA 5'-capping enzyme, which is the guanylyltransferase from Chlorella virus PBCV1, in the gel as alignment medium; the enzyme was analyzed in the stretched 6% (w/w) gel of 50% acrylamide/50% acrylate (alignment medium) at 20° C. (293K); and in the Figure, "I" represents data acquired in an isotropic state, while "A" represents data acquired in an aligned state.

PBCV1-CE was oriented with regard to the magnetic field by putting 0.5 mM PBCV1-CE (200 mM potassium phosphate, pH 7.6 labeled with $^2H/^{15}N$ into a 6% (w/w) gel of 50% acrylamide/50% acrylate (alignment medium) (FIG. 3) stretched by about 2.5 times. 5 mM pyrophosphoric acid, an activity inhibitor, was added to the sample solution. TROSY measurement was performed at 20° C. (FIG. 4). TROSY shift change dependent on molecular orientation was observed as a deviation from the TROSY signal in a state of normal solution to $^{15}N$ axis side for a TROSY signal of PBCV1-CE in the alignment medium. Based on a TROSY shift change which showed sufficient separation of signals for 51 residues (N-terminal domain, 23 residues, C-terminal domain, 28 residues) and orientation tensor of each domain was determined.

Analysis was performed based on the structures having two different domain orientations of PBCV1-CE (open type and closed type) which were found in crystal structure to confirm accuracy of the results of provided relative domain orientation. Two residues of N terminal domain were removed from analysis in order to exclude influence of structural change in partial domain in the analysis based on crystal structure of closed type.

(Molecular Orientation Analysis)

According to the process of the present invention, molecular orientation between domains was analyzed with data of open type structure. $\Delta\delta$trosy value was obtained and Saupe order matrix elements were determined similarly as in Example 2 and Euler angles α, β and γ in the absence of nucleotide were determined.

PBCV1-CE has a clear domain structure in its conformation. Orientation tensor of each domain was determined from a change of the TROSY signal which is dependent on orientation and respectively derived from each of the domains (small domain) comprising 239-311 as well as a domain (large domain) comprising 15-222 with an amino acid residue number. As a result, as show in table 3, the Euler angles which express a tilt of the molecular orientation axis from the molecule coordinate axis are (α=95.9°, β=123.1°, γ=96.2°, Q-factor=0.38) for a large domain (N-terminal) and (α=98.4°, β=114.7°, γ=165.4°, Q-factor=0.45) for a little domain (C-terminal).

TABLE 3

| | Euler angles [°] | | | Q-factor |
|---|---|---|---|---|
| | α | β | γ | |
| N-terminal | 95.9 | 123.1 | 96.2 | 0.38 |
| C-terminal | 98.4 | 114.7 | 165.4 | 0.45 |

Figure 5:
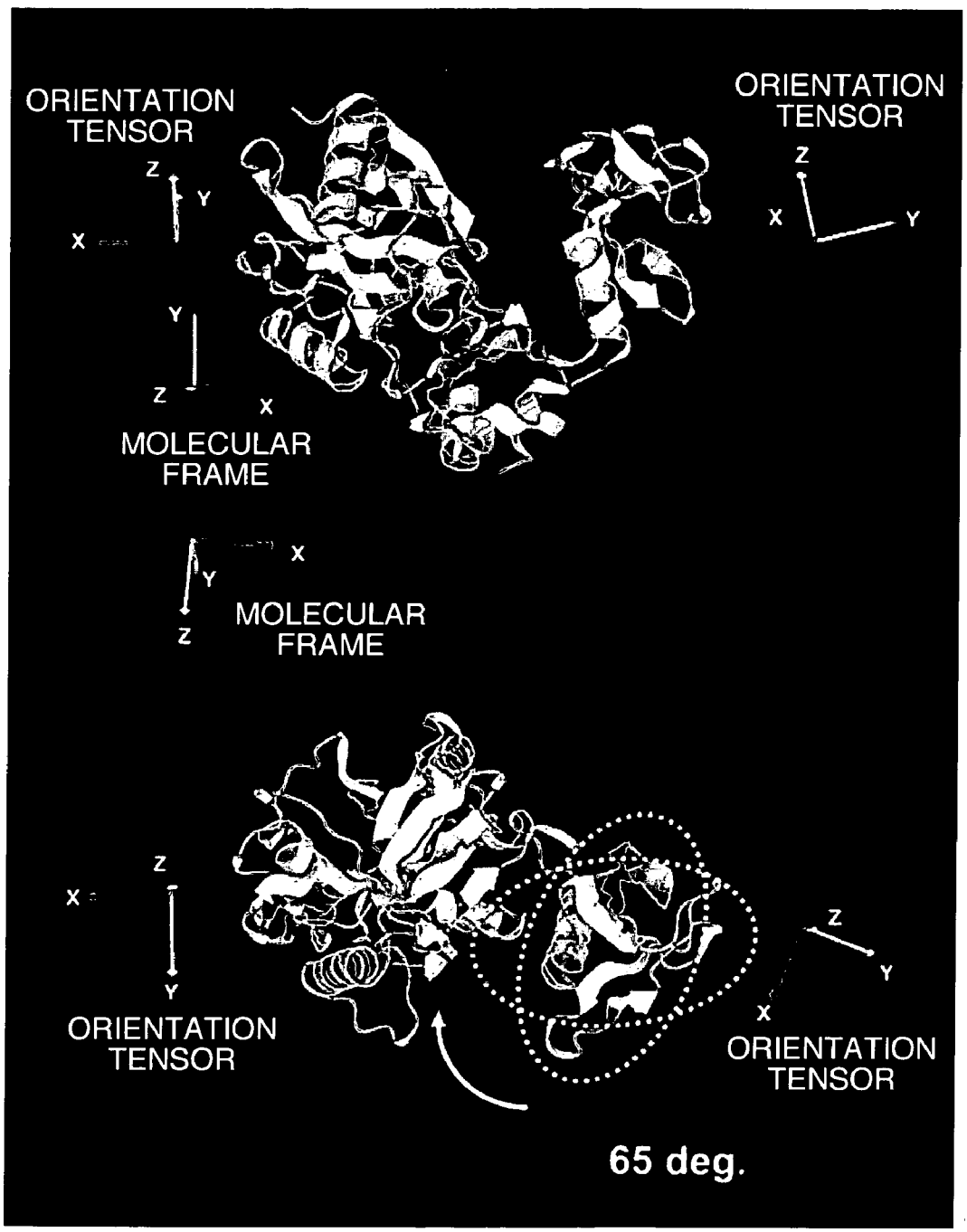
FIG. 5 shows the results of analysis based on an open crystal structure, where orientation tensors were determined from 23 residues in the N-terminal domain (large domain) and 28 residues in the C-terminal domain (small domain)
Figure 6:
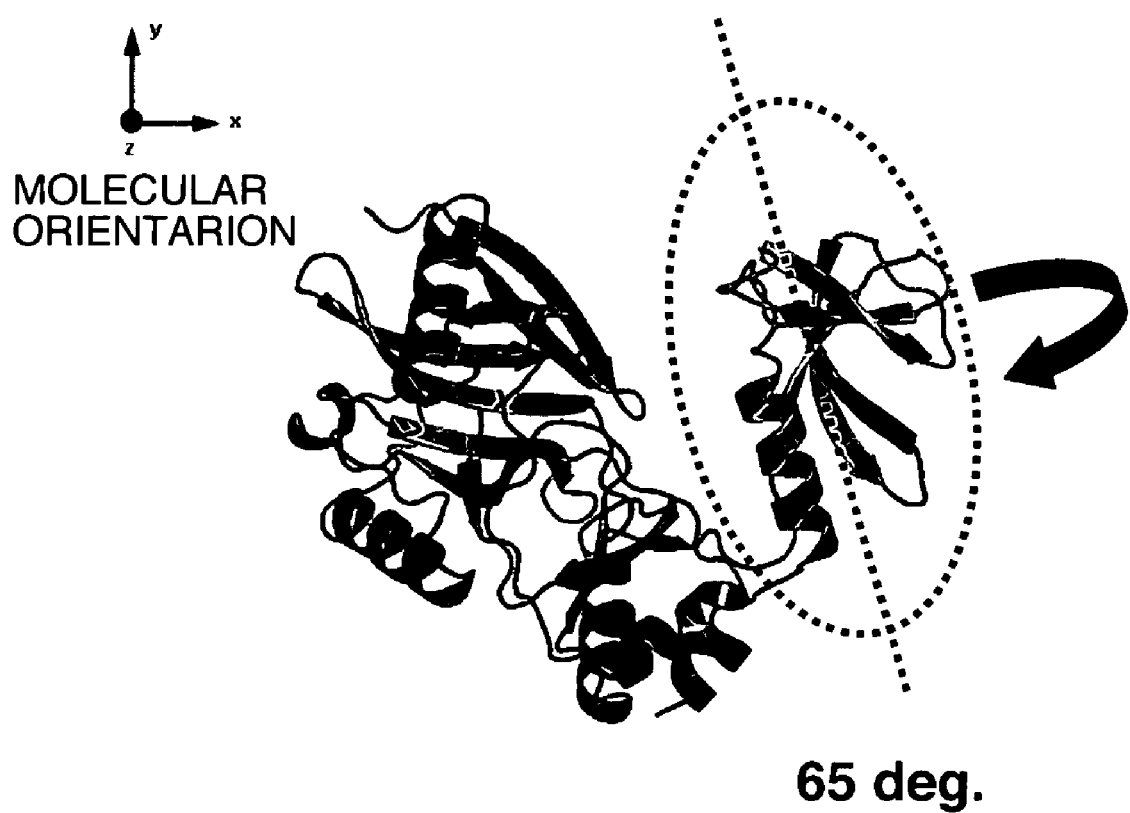
FIG. 6 shows the results of analysis based on an open crystal structure, where orientation tensors were determined from 23 residues in the N-terminal domain (large domain) and 28 residues in the C-terminal domain (small domain)

Molecular orientation axes of each domain are as shown in FIG. 5 and FIG. 6. The relative orientation of domain was determined by rotating the small domain so that two orientation axes agree with each other, and it became clear that the small domain has rotated at about 65° compared with the crystal structure from orientation tensor of each domain.

Figure 7:
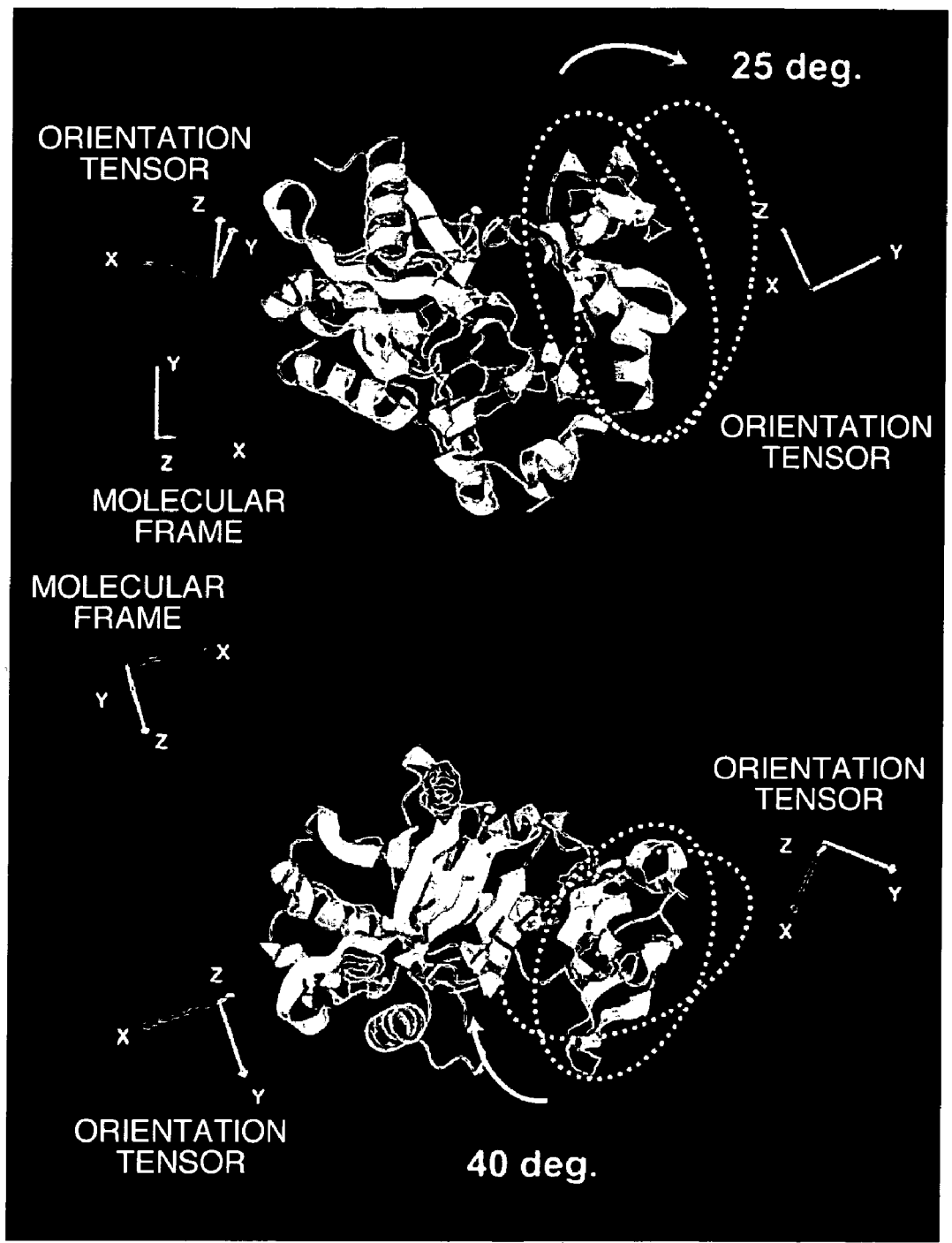
FIG. 7 shows the results of analysis based on a closed crystal structure, where orientation tensors were determined from 21 residues in the N-terminal domain (large domain) and 28 residues in the C-terminal domain (small domain)
Figure 8:
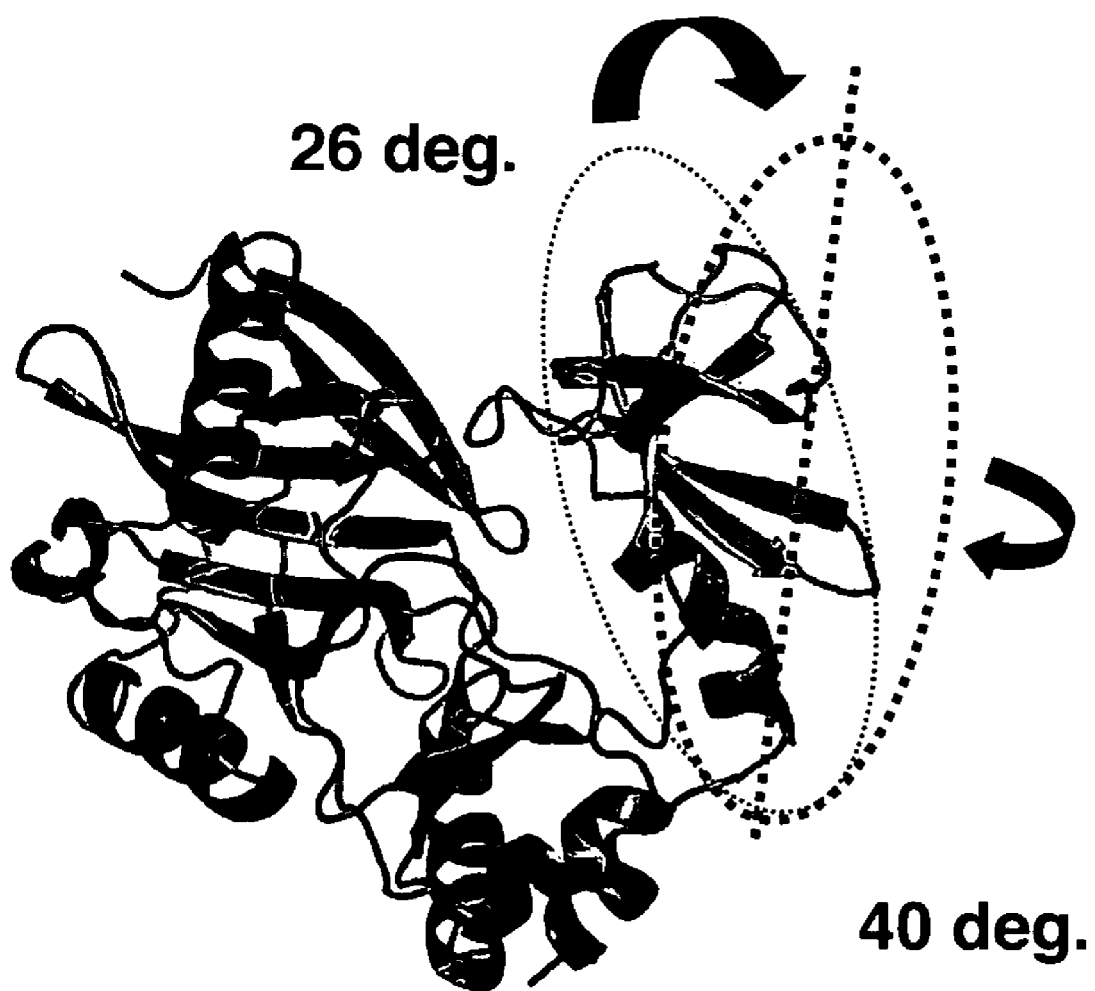
FIG. 8 shows the results of analysis based on a closed crystal structure, where orientation tensors were determined from 21 residues in the N-terminal domain (large domain) and 28 residues in the C-terminal domain (small domain).

Structure which had another domain orientation (closed type) of PBCV1-CE found in crystal structure was used to confirm the accuracy of the results of relative domain orientation provided by using an open type structure. The results are shown in the following Table 4 and FIG. 7 and FIG. 8.

TABLE 4

| | Euler angles [°] | | | Q-factor |
|---|---|---|---|---|
| | α | β | γ | |
| N-terminal | 77.2 | 124.3 | 87.1 | 0.46 |
| C-terminal | 105.4 | 115.2 | 150.3 | 0.42 |

The relative orientations between domains determined as a result of method of analysis of the present invention are similar for open type and closed type and, therefore, accuracy of relative orientation between determined domains was confirmed.

Using a similar method, Euler angles α, β and γ are determined in the presence of GTP and in the presence of ATP, respectively. Furthermore, from this Euler angles, DOCs at the time of GTP addition and ATP addition were calculated. These DOCs are an index of structural change at the time of GTP addition and at the time of ATP addition.

EXAMPLE 4

(Screening of Agonistic Lead Compounds for a Protein)

Search for a new agonist and/or antagonist of protein is important for the production of a new drug. Particularly, a new agonist could be used as an agonistic lead compound, but the conventional technique was inadequate for identification of agonistic lead compounds.

Therefore, screening of agonistic lead compound is performed according to the present invention. mRNA5'-capping enzyme used in Example 3 is used as a model.

Since it is believed that an agonistic lead compound produces a structural change which is similar to GTP activating mRNA5'-capping enzyme in mRNA5'-capping enzyme, screening is performed as follows.

Information on an orientation of mRNA5'-capping enzyme is obtained under a similar condition as in Example 3 except that an experiment is performed in which one of the candidate compounds is substituted for GTP. Nucleotide analogs, particularly GTP analogs and ATP analogs can be used as a candidate compound. DOS was calculated from information on an orientation in the presence of GTP and information on an orientation in the presence of the candidate compound.

A compound having small DOS value is selected as an agonistic lead compound from plural candidate compounds.

EXAMPLE 5

(Identification of Binding Site of an Agonistic Lead Compound Selected from Candidate Compounds)

When an agonistic lead compound has been selected, binding site of the agonistic lead compound can be identified. In this example, a compound which produced the smallest DOS value in Example 4 is used and experiment is performed as follows.

Performing assignment of two-dimensional TROSY NMR spectrum to amino acid residues in the absence of the candidate compound used in Example 4 according to a conventional process.

Comparing two dimensional TROSY NMR spectrum in a domain of the protein in the presence of the candidate compound and two dimensional TROSY NMR spectrum in the absence of the candidate compound. A spectral change is detected from the comparison. An amino acid residue corresponding to the changed spectrum is identified as a binding site of the agonistic lead compound from the results of the above assignment.

EXAMPLE 6

(Determination of Affinity of Compound to Target Protein)

In the present invention, affinity of a compound to the target protein can be determined, for example, by the following method.

Assignment of two-dimensional TROSY NMR spectrum to amino acid residues in the absence of a candidate compound used in Example 4 is carried out according to a conventional process.

Two dimensional TROSY NMR spectrum in a domain of the protein in the presence of the compound and two dimensional TROSY NMR spectrum in the absence of the compound are compared. A spectral change is detected by the comparison. An amino acid residue corresponding to the spectral change is identified from the results of the above assignment.

The spectrum corresponding to the identified amino acid appears in different positions in the absence of the compound and in the presence of the compound. However, there is a case where the spectrum corresponding to the identified amino acid detected in the absence of a compound remains even in the presence of the compound depending on the type of the compound. The reason why the spectrum corresponding to a single amino acid residue doubly exists is that a compound bound to the protein and a compound not bound to the protein are both present in the solution of two-dimensional TROSY NMR measurement. The ratio of intensity of spectrum corresponding to this doubly existing single amino acid residue relates to the abundance ratio with compound binding protein and compound non-binding protein. Therefore, the ratio of intensity of this double spectrum is an index of affinity of a compound tested and the protein. Based on this principle, the relative affinity of the compound can be measured as follows:

identifying the amino acid residue which a compound binds following Example 5;

performing the NMR measurement in the presence of Compound A and with regard to the spectrum corresponding to the amino acid to which the compound binds, calculating the ratio of (spectrum appearing at a position detected only in the presence of Compound A)/(spectrum which remains at a position detected in the absence of compound);

performing the NMR measurement in the presence of Compound B and with regard to the spectrum corresponding to the amino acid to which the compound binds, calculating the ratio of (spectrum appearing at a position detected only in the presence of Compound B)/(spectrum which remains at a position detected in the absence of compound); and comparing these ratios for Compounds A and B, and judging that a compound having a larger ratio has a larger affinity to the target protein.

INDUSTRIAL APPLICABILITY

Screening of ligand, agonist, antagonist of a protein becomes rapid and easy by detecting a structural change of the protein occurring by binding of a compound. Furthermore, detection of structural change enables to screen a candidate compound of a new drug using as an index whether an active structure of the target protein is induced or not.

The invention claimed is:

1. A computer-implemented method of measuring a structural change in a protein when the protein is contacted with a compound, comprising the steps of:
  (a) selecting a domain in the protein using an input device;
  (b) providing information on an orientation of the domain when the protein is not in contact with the compound;
  (c) providing information on an orientation of the domain when the protein is in contact with the compound, by:
    (i) providing known atomic coordinates for the domain,
    (ii) providing axial variations of NMR signals, which are generated from the protein in contact with the compound in the presence of a liquid crystalline material by two-dimensional TROSY NMR spectroscopy and depend on an orientation angle of the protein and compound in a magnetic field,
    (iii) determining Saupe order matrix elements for the domain from the atomic coordinates for the domain and the axial variations of NMR signals using a computer processor, and
    (iv) diagonalizing the Saupe order matrix elements to produce information on an orientation of the domain using the processor; and
  (d) measuring the structural change in the protein using the processor by a difference between the information on an orientation provided in step (b) and the information on an orientation provided in step (c),
  wherein a structural change in the protein when the protein and the compound are contacted is digitized as degree of orientational change by:
    (v) providing directions of orientation tensor axes by a first three unit vectors perpendicular to each other, by using the information on an orientation of the domain in the protein before the protein is contacted with the compound, wherein the first three unit vectors are expressed by $$\vec{e}_{fx}, \vec{e}_{fy}, \vec{e}_{fz},$$

(vi) providing directions of orientation tensor axes by a second three unit vectors perpendicular to each other, by using the information on an orientation of the domain in the protein after the protein is contacted with the compound, wherein the second three unit vectors are expressed by $$\vec{e}_{bx}, \vec{e}_{by}, \vec{e}_{bz},$$

(vii) denoting respective angles between the individual first unit vectors and the individual second unit vectors by a, b and c, and
    (viii) giving a degree of orientational change by the following equation:

degree of orientational change=$a^2+b^2+c^2$.

2. The method of measurement according to claim 1, wherein the step (b) is a step of:
  (b) providing information on an orientation of the domain when the protein is not in contact with the compound, by:
    (ix) providing known atomic coordinates for the domain,
    (x) providing axial variations of NMR signals, which are generated from the protein in no contact with the compound in the presence of the liquid crystalline material by two-dimensional TROSY NMR spectroscopy and depend on the orientation angle of the protein and compound in the magnetic field,
    (xi) determining Saupe order matrix elements for the domain from the atomic coordinates for the domain and the axial variations of NMR signals using the processor, and
    (xii) diagonalizing the determined matrix to produce the information on an orientation of the domain.

3. The method of measurement according to claim 1, wherein the step (b) is a step of
  (b) providing the information on an orientation of the domain from the atomic coordinates provided previously when the protein was not in contact with the compound.

4. The method of measurement according to claim 1, wherein in the step (c), the axial variations of NMR signals, which are generated by two-dimensional TROSY NMR spectroscopy and depend on the orientation angle of the molecules in the magnetic field, are variations along a $^{15}$N axis.

5. The method of measurement according to claim 4, wherein the Saupe order matrix elements in (iii) are determined by:
  with respect to a kth pair of $^{15}$N nuclear spins in the domain,
  providing $\phi^k_i$ as a vector angle of an N—H bond having the kth pair of spins in the domain to an ith molecular axis,
  providing $\phi_{kj}$ as a vector angle of an N—H bond having the kth pair of spins in the domain to a jth molecular axis,
  setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å,
  determining as $\delta_{ij}$ a tensor value for chemical shift anisotropy of a $^{15}$N nucleus in an arbitrary residue of the protein using the processor, and
  determining the Saupe order matrix elements $S_{ij}$ defining the molecular orientation with respect to the magnetic field using the processor, by contacting the protein with the compound in the presence of the liquid crystalline material, providing Δδtrosy(k) for the kth pair of $^{15}$N nuclear spins of the protein by two-dimensional TROSY NMR spectroscopy, and using the Δδtrosy(k) together with the following equation (1):

Δδtrosy(k)=$\Sigma S_{ij}\{0.5\,D^0_{nh}\cos\phi^k_i\cos\phi^k_j+(2/3)\delta_{ij}\}$     (1)

i,j=x, y, z.

6. The method of measurement according to claim 2, wherein in the step (b), the axial variations of NMR signals, which are generated by two-dimensional TROSY NMR spectroscopy and depend on the orientation angle of the molecules in the magnetic field, are variations along a $^{15}N$ axis.

7. The method of measurement according to claim 6, wherein the Saupe order matrix elements in (vii) are determined by:
with respect to a kth pair of $^{15}N$ nuclear spins in the domain,
providing $\phi^k_i$ as a vector angle of an N—H bond having the kth pair of spins in the domain to an ith molecular axis,
providing $\phi^k_j$ as a vector angle of an N—H bond having the kth pair of spins in the domain to a jth molecular axis,
setting a static dipolar coupling $D^0_{nh}$ at 23.0 kHz for a length of the N—H bond of 1.02 Å, or setting a static dipolar coupling $D^0_{nh}$ at 21.7 kHz for a length of the N—H bond of 1.04 Å,
determining as $\delta_{ij}$ a tensor value for chemical shift anisotropy of a $^{15}N$ nucleus in an arbitrary residue of the protein, and
determining the Saupe order matrix elements $S_{ij}$ defining the molecular orientation with respect to the magnetic field, by making no contact of the protein with the compound in the presence of the liquid crystalline material, providing $\Delta\delta\text{trosy}(k)$ for the kth pair of $^{15}N$ nuclear spins by two-dimensional TROSY NMR spectroscopy, and using the $\Delta\delta\text{trosy}(k)$ together with the following equation (1):

$$\Delta\delta\text{trosy}(k)=\Sigma S_{ij}\{0.5\, D^0_{nh}\cos\phi^k_i\cos\phi^k_j+(2/3)\delta_{ij}\} \quad (1)$$

i,j=x, y, z.

8. The method according to claim 2, further comprising a step of identifying a position on the protein to which the compound is bound.

9. The method according to claim 8, wherein the step of identifying a position on the protein to which the compound is bound is carried out by comparing a two-dimensional TROSY NMR spectrum which comprise the information provided in the step (b) with a two-dimensional TROSY NMR spectrum which comprises the information provided in the step (c) to detect a spectral change, and identifying an amino acid residue in the protein which has induced the spectral change.

10. The method according to claim 1, wherein the liquid crystalline material comprises a mixture selected from the group consisting of:
a mixture of dimyristoylphosphatidylcholine (DMPC) and dihexanoylphosphatidylcholine (DHPC),
a mixture of dimyristoylphosphatidylcholine (DMPC), dihexanoylphosphatidylcholine (DHPC), and sodium dodecyl sulfate (SDS),
a mixture of dimyristoylphosphatidylcholine (DMPC), dihexanoylphosphatidylcholine (DHPC), and cetyltrimethylammonium bromide (CTAB),
a mixture of 1,2-di-O-dodecyl-sn-glycero-3-phosphocholine(DIODPC) and 3-(cholamidepropyl)-dimethylammonio-2-hydroxy-1-propane sulfate (CHAPS),
a mixture of n-alkyl-poly(ethyleneglycol)/n-alkylalcohol,
filamentous phage,
a mixture of cetylpyridinium chloride(CPCl)-hexanol-NaCl,
a mixture of cetylpyridinium bromide(CPBr)-hexanol-NaCl,
a purple membrane fragment of Halobacterium species,
microcrystalline cellulose, and
polyacrylamide gel.

11. The method according to claim 10, wherein the liquid crystalline material is the mixture of 7.5%(w/v) composed of dimyristoylphosphatidylcholine (DMPC), dihexanoylphosphatidylcholine (DHPC), and cetyltrimethylammonium bromide (CTAB).

* * * * *